(12) United States Patent
Magnussen et al.

(10) Patent No.: US 11,992,309 B2
(45) Date of Patent: *May 28, 2024

(54) WIDEBAND ACOUSTIC IMMITTANCE MEASUREMENT APPARATUS

(71) Applicant: Natus Medical Incorporated, Pleasanton, CA (US)

(72) Inventors: Camilla Magnussen, Glostrup (DK); Ask Bojesen, Glostrup (DK)

(73) Assignee: Natus Medical Incorporated, Middleton, WI (US)

( * ) Notice: Subject to any disclaimer, the term of this patent is extended or adjusted under 35 U.S.C. 154(b) by 407 days.

This patent is subject to a terminal disclaimer.

(21) Appl. No.: 17/305,102

(22) Filed: Jun. 30, 2021

(65) Prior Publication Data
US 2021/0321911 A1    Oct. 21, 2021

Related U.S. Application Data

(63) Continuation of application No. 16/045,981, filed on Jul. 26, 2018, now Pat. No. 11,076,780.

(30) Foreign Application Priority Data

Aug. 3, 2017   (EP) ..................................... 17184747

(51) Int. Cl.
*A61B 5/00* (2006.01)
*A61B 5/12* (2006.01)

(52) U.S. Cl.
CPC ............ *A61B 5/126* (2013.01); *A61B 5/7235* (2013.01)

(58) Field of Classification Search
CPC .................. A61B 5/126; A61B 5/7235; A61B 2562/0204; A61B 5/4803; A61B 5/7282;
(Continued)

(56) References Cited

U.S. PATENT DOCUMENTS 8,989,830 B2 *   3/2015   LeBoeuf .............. A61B 5/1107
                                                    600/310
9,107,620 B2 *   8/2015   Ito .......................... A61B 5/123
(Continued)

OTHER PUBLICATIONS

U.S. Appl. No. 16/045,981, filed Jul. 26, 2018.

*Primary Examiner* — May A Abouelela
(74) *Attorney, Agent, or Firm* — Daniel C. Pierron; Widerman Malek, PL

(57) ABSTRACT

A wideband acoustic immittance measurement apparatus including an ear probe having an acoustic output port for emitting sound into an ear canal and an acoustic input port for receiving sound from the ear canal, a loudspeaker that is acoustically connected with the acoustic output port, a microphone acoustically connected with the acoustic input port for generating an audio signal as a function of sound received at the acoustic input port, and a processor for controlling the loudspeaker to emit sound spanning a frequency range and receiving the audio signal of the microphone, determining a complex acoustic admittance $Y(f)=G(f)+jB(f)$ as a function of frequency f based on the emitted sound and the received audio signal, and identifying at least one middle ear resonance based on both the real and imaginary part of the determined acoustic admittance as a function of frequency f.

20 Claims, 8 Drawing Sheets

(58) Field of Classification Search
CPC ......... G10L 15/22; G10L 15/07; G10L 15/08; G10L 2015/225; G10L 19/008
See application file for complete search history.

(56) References Cited

U.S. PATENT DOCUMENTS

| | | | |
|---|---|---|---|
| 9,744,358 B2* | 8/2017 | Hehrmann | A61N 1/0541 |
| 9,750,437 B2* | 9/2017 | Schwarz | A61B 5/686 |
| 10,413,197 B2* | 9/2019 | LeBoeuf | A61B 5/0059 |
| 10,542,961 B2* | 1/2020 | Barsimantov | A61B 7/00 |
| 10,582,328 B2* | 3/2020 | Milevski | H04S 7/304 |
| 2004/0225207 A1* | 11/2004 | Bae | A61B 5/02416 |
| | | | 374/E13.003 |
| 2005/0123146 A1* | 6/2005 | Voix | A61F 11/08 |
| | | | 381/328 |
| 2008/0146890 A1* | 6/2008 | LeBoeuf | A61B 7/003 |
| | | | 600/300 |
| 2008/0146892 A1* | 6/2008 | LeBoeuf | A61B 5/0022 |
| | | | 600/300 |
| 2010/0292585 A1* | 11/2010 | Uenishi | A61B 5/02225 |
| | | | 600/300 |
| 2013/0303941 A1* | 11/2013 | Porges | A61B 5/125 |
| | | | 600/559 |
| 2014/0180039 A1* | 6/2014 | LeBoeuf | A61B 5/02055 |
| | | | 600/324 |
| 2014/0288441 A1* | 9/2014 | Luna | A61B 5/053 |
| | | | 600/509 |
| 2015/0215719 A1* | 7/2015 | Turgul | H04R 1/1091 |
| | | | 381/58 |
| 2015/0265189 A1* | 9/2015 | Allen | A61B 5/126 |
| | | | 600/559 |
| 2015/0305678 A1* | 10/2015 | Reinholdt-Nielsen | |
| | | | A61B 5/126 |
| | | | 600/559 |
| 2015/0350759 A1* | 12/2015 | Shin | H04R 1/1016 |
| | | | 381/58 |
| 2015/0351688 A1* | 12/2015 | Just | A61B 5/6817 |
| | | | 600/407 |
| 2016/0014532 A1* | 1/2016 | Nielsen | A61B 5/126 |
| | | | 381/60 |
| 2016/0066851 A1* | 3/2016 | Inagaki | H04R 17/00 |
| | | | 600/300 |
| 2016/0220155 A1* | 8/2016 | Bojesen | A61B 5/126 |
| 2017/0312135 A1* | 11/2017 | Parkins | H04R 1/1083 |
| 2017/0332977 A1* | 11/2017 | Dalhoff | A61B 5/125 |
| 2019/0038188 A1* | 2/2019 | Lodwig | A61B 5/7214 |
| 2020/0074995 A1* | 3/2020 | Rosenberg | G10L 15/20 |

\* cited by examiner

WIDEBAND ACOUSTIC IMMITTANCE MEASUREMENT APPARATUS

RELATED APPLICATIONS

This application is a continuation application of and claims priority under 35 U.S.C. § 120 of U.S. patent application Ser. No. 16/045,981 filed on Jul. 26, 2018 and titled Wideband Acoustic Immittance Measurement Apparatus, which in turn claims priority under 35 U.S.C. § 120 of European Patent Application Serial No. 17184747.8, now European Patent No. 3437551, issued Jul. 31, 2019 filed on Aug. 3, 2017 and titled Wideband Acoustic Immittance Measurement Apparatus. The contents of these applications are incorporated herein by reference.

FIELD OF THE INVENTION

This invention relates generally to the field of acoustic immittance measuring, and more particularly to a system and method for wideband acoustic immittance measurement.

BACKGROUND OF THE INVENTION

The middle ear is the portion of the ear internal to the tympanic membrane and external to the oval window of the inner ear. The middle ear comprises the tympanic membrane also denoted the ear drum, and the ossicles, i.e. the malleus, incus and stapes. The ossicles transfer vibrations of the tympanic membrane into waves in the fluid and membranes of the cochlea in the inner ear.

The primary function of the middle ear is to efficiently transfer acoustic waves in the ear canal incident on the tympanic membrane to fluid-membrane waves within the cochlea. The middle ear efficiency peaks at a frequency of app. 1 kHz. The combined transfer function of the outer ear and middle ear of humans results in peak sensitivity to frequencies between 1 kHz and 3 kHz.

Tympanometry, sometimes also denoted immittance testing, is a well-known method of examining and diagnosing the middle ear. Tympanometry involves recording changes in middle ear admittance, while static pressure in the ear canal is varied.

In order to perform tympanometry, an ear probe is inserted in the ear canal in such a way that an air tight seal of the ear canal is provided. The ear probe has a loudspeaker for emission of sound, typically a 226 Hz pure tone, towards the tympanic membrane under varying static pressure in the ear canal inside the seal. The emitted sound causes vibration of the tympanic membrane and the ossicles of the middle ear, which in turn results in the conscious perception of hearing. Some of the emitted sound is reflected and picked up by a microphone of the ear probe. Typically, the ear probe varies the static pressure from −400 daPa to 200 daPa with 50-600 daPa/second sweep pressure rate (1 daPa=10 Pa).

The tympanometer determines acoustic admittances of the middle ear based on the microphone signal and plots the determined acoustic admittances as a function of static pressure thereby forming a so-called tympanogram.

Normally, the static pressure in the ear canal is the same as ambient pressure, and also under normal conditions, the static pressure in the middle ear is approximately the same as ambient pressure since the Eustachian tube opens periodically to ventilate the middle ear and to equalize pressure. In a healthy individual, the maximum sound is transmitted through the middle ear when the static pressure in the ear canal is equal to the pressure in the middle ear also denoted the tympanic peak pressure TPP.

In multi-frequency tympanometry, the frequency of the pure tone is also varied. With the so-called sweep pressure method, the frequency of the pure tone is held constant while the static pressure is varied; and with the so-called sweep frequency method, the static pressure is held constant at specified intervals while the frequency of the pure tone is varied.

Experimental data have shown that middle ear pathologies alter tympanometric shapes and shift the resonance frequency of the middle ear. For example, increases in stiffness due to otosclerosis can shift middle ear resonance to a higher than normal frequency, and increases in mass (or lack of stiffness) due to ossicular discontinuity can shift middle ear resonance to a lower than normal frequency.

In order to perform tympanometry, the ear probe is connected with a cable to a so-called tympanometer, which controls the tympanometry procedure. The measurement results are recorded by the tympanometer.

The cable typically includes electrical conductors for interconnection of the microphone and a loudspeaker and switches and possible indicators, respectively, of the ear probe.

The cable also has an air conduit for interconnection with a pump of the tympanometer for control of the static pressure in the ear canal subjected to the tympanometry test.

A hand-held ear probe may be used for screening purposes, while an ear probe that is retained more securely in or at the ear canal of a human is typically preferred for clinical tests.

SUMMARY OF THE INVENTION

To minimize the limitations found in the existing systems and methods, and to minimize other limitations that will be apparent upon the reading of the specifications, preferred embodiment of the present invention provides a system and method for real time removal of reflections from an image.

Utilizing conventional multi-frequency tympanometry to diagnose the middle ear is cumbersome due to the large number of measurements that have to be performed and the resultant abundance of data that has to be collected and interpreted by the audiologist.

Thus, there is a need for an improved apparatus for accurately characterizing the middle ear based on a reduced number of measurements and providing data that are easy to interpret by the audiologist.

Further, there is a need for an improved apparatus for accurately characterizing the middle ear in a robust and direct way.

Thus, a new wideband acoustic immittance measurement apparatus for determination of wideband acoustic immittance $F(f)$ in an ear of a human is provided for characterization of the middle ear of the human.

The new wideband acoustic immittance measurement apparatus is configured for determination of wideband acoustic immittance $F(f)$ with an ear probe inserted in the ear of the human, and for characterizing the middle ear by identifying one or more middle ear resonances, if any, based on the determined wideband acoustic immittance $F(f)$.

The criteria for identification of a middle ear resonance are based on the realisation that middle ear resonances have characteristics that are similar to the characteristics of the resonance of a Helmholtz resonator, or network of Helmholtz resonators.

A middle ear resonance may be identified based on a comparison of characteristics of the determined wideband acoustic immittance F(f) with corresponding characteristics at the resonance frequency $f_0$ of the Helmholtz resonator, or one resonance frequency $f_0$ of the network of Helmholtz resonators, of the corresponding wideband acoustic immittance $F_H(f)$ determined for the Helmholtz resonator, or network of Helmholtz resonators.

An overview of wideband acoustic immittance measurements and reviews of the relationships among different acoustic immittance measurements, including acoustic impedance, acoustic admittance, acoustic reflectance, and acoustic absorbance, are provided by: John J. Rosowski, Stefan Stenfelt, and David Lilly: "An Overview of Wideband Immittance Measurements Techniques and Terminology: You Say Absorbance, I Say Reflectance", Ear and Hearing 2013; 34; 9S-16S.

With the new wideband acoustic immittance measurement apparatus, acoustic immittance measurements are performed with an ear probe positioned in the ear of the human for emission of sound towards the tympanic membrane at the end of the ear canal.

Thus, the new wideband acoustic immittance measurement apparatus for determination of wideband acoustic immittance F(f) in the ear of the human, comprises
- an ear probe for insertion in the ear of the human and having
  - an acoustic output port for emission of sound into the ear of the human, and
  - an acoustic input port for reception of sound in the ear of the human, and
- a loudspeaker that is arranged for acoustical connection with the acoustic output port of the ear probe for conversion of an output audio signal into the sound, and
- a microphone that is arranged for acoustical connection with the acoustic input port of the ear probe for generation of an input audio signal as a function of sound pressure at the acoustic input port.

The ear probe may accommodate one of, or both of, the loudspeaker and the microphone.

Thus, the new wideband acoustic immittance measurement apparatus for determination of wideband acoustic immittance F(f) in the ear of the human, may comprise an ear probe for insertion in an ear canal of the human and having the loudspeaker for conversion of the output audio signal into the sound, and the microphone for generation of the input audio signal as a function of sound pressure at the microphone.

The new wideband acoustic immittance measurement apparatus may have a housing separate from the ear probe for accommodation of one of, or both of, the loudspeaker and the microphone.

When operated, the housing is interconnected with the ear probe with a cable that contains electrical wires for interconnection with the microphone and/or the loudspeaker when accommodated in the ear probe and that contains air conduits for acoustic interconnection of the microphone and/or the loudspeaker when accommodated in the housing with the respective acoustic input port and acoustic output port of the ear probe.

To determine acoustic immittance of the middle ear, the sound delivery system of the wideband acoustic immittance measurement apparatus must be known.

Calibration of acoustic immittance measurements may be performed as disclosed in:

Allen, J. B. (1985). Measurement of eardrum acoustic impedance. Peripheral Auditory Mechanism, edited by J. Allen, J. Hall, A. Hubbard, S. Neely, and A. Tubis (Springer-Verlag, New York), and Keefe, D. H. (1984). Acoustical wave propagation in cylindrical ducts: transmission line parameter approximation for isothermal and nonisothermal boundary conditions. Journal Acoustical Society of America, (January), and Keefe, D. H., Ling, R., & Bulen, J. (1991). Method to measure acoustic impedance and reflection coefficient. Journal Acoustical Society of America, 470-485.

One example of calibration of wideband acoustic immittance measurements are explained in more detail below with reference to FIG. 1; however, other ways of performing calibration of wideband acoustic immittance measurements are well-known in the art.

FIG. 1 shows a Thévenin equivalent circuit for an immittance measurement performed with an ear probe.

As shown in FIG. 1, the sound source of the ear probe, or connected to the ear probe, is modelled by an ideal sound pressure generator $P_0$, i.e. a sound pressure generator with zero source impedance, in series with a source impedance $Z_0$, which is connected in series with the acoustic load Z.

The sound pressure P at the acoustic output port of the ear probe is determined by:

$$P = P_0 \frac{Z}{Z_0 + Z} \quad (1)$$

wherein

P is the sound pressure measured by the microphone of the ear probe, or connected to the ear probe, Z is the acoustic impedance of the acoustic load, e.g. the ear of the human, and $P_0$ and $Z_0$ are the Thévenin sound source parameters of the ear probe.

It is implicit that all the quantities are complex functions of frequency f so that equation (1) may be written:

$$P(f) = P_0(f) \frac{Z(f)}{Z_0(f) + Z(f)} \quad (2)$$

where f is the frequency.

Measurements of sound pressure P at two different acoustic loads with known acoustic impedances $Z_A$ and $Z_B$ allow the calculation of the two equivalent circuit parameters of the sound source $P_0$ and $Z_0$.

The parameters of the sound source $P_0$ and $Z_0$ are often determined by measurements with more than two cavities, e.g. tubes, with known acoustic impedances $Z_i$:

$$P_i = P_0 \frac{Z_i}{(Z_0 + Z_i)}, i = 1, \ldots, N \quad (3)$$

resulting in an overdetermined system. One way to estimate the parameters $P_0$ and $Z_0$ of the sound source in an overdetermined equation system is to utilize a least-squares approach.

Upon calibration of the parameters $P_0$ and $Z_0$ of the ear probe, the complex acoustic impedance Z is determined by measuring the sound pressure P with the microphone of the ear probe:

$$Z = Z_0 \frac{P}{P_0 - P} \quad (4)$$

Based on the determined acoustic impedance Z, other acoustic immittances may be derived, such as:

The complex acoustic admittance Y (typical in units of mmho):

$$Y = \frac{1}{Z} \quad (5)$$

The complex acoustic reflectance Γ (dimensionless):

$$\Gamma = \frac{Z - Z_c}{Z + Z_c} \quad (6)$$

where $Z_c$ is the characteristic acoustic impedance of the ear canal at the acoustic output port of the ear probe:

$$Z_c = \frac{\rho c}{A} \quad (7)$$

where:
A is the area of the cross-section of the ear canal at the acoustic output port of the ear probe,
ρ is the density of air, and
c is the speed of sound.

The acoustic energy reflectance ER:

$$ER = |\Gamma|^2 \quad (8)$$

The acoustic energy absorbance:

$$EA = 1 - ER = 1 - |\Gamma|^2 \quad (9)$$

It is implicit that all the immittances are complex functions F(f) of the frequency f.

The wideband acoustic immittance F(f) determined by the wideband acoustic immittance measurement apparatus, may be any function that can be determined based on measurement with the ear probe, including the acoustic immittances mentioned above, namely acoustic admittance Y(f), acoustic impedance Z(f), acoustic reflectance Γ(f), acoustic energy reflectance ER(f), and acoustic energy absorbance EA(f).

Thus, the new wideband acoustic immittance measurement apparatus may determine complex acoustic admittance $Y(f) = G(f) + j*B(f) = |Y(f)|e^{j\phi(f)}$ with the ear probe positioned in the ear of the human.

The real part of the acoustic admittance Y(f) is the conductance G(f), and the imaginary part of the acoustic admittance Y(f) is the susceptance B(f).

|Y(f)| is the magnitude of the acoustic admittance Y(f), in short the acoustic admittance magnitude; and φ(f) is the phase of the acoustic admittance Y(f), in short the acoustic admittance phase.

The new wideband acoustic immittance measurement apparatus may provide characterization of the middle ear of a human based on the determined complex acoustic admittance Y(f), e.g. based on the conductance G(f) and the susceptance B(f) of the acoustic admittance Y(f); or, based on the acoustic admittance magnitude |Y(f)| and acoustic admittance phase φ(f).

Correspondingly, the new wideband acoustic immittance measurement apparatus may determine complex acoustic impedance $Z(f) = R(f) + j*X(f) = |Z(f)|e^{j\theta(f)}$ with the ear probe positioned in the ear of the human.

The real part of the acoustic impedance Z(f) is the resistance R(f), and the imaginary part of the acoustic impedance Z(f) is the reactance X(f).

|Z(f)| is the magnitude of the acoustic impedance Z(f), in short the acoustic impedance magnitude, and θ(f) is the phase of the acoustic impedance Z(f), in short the acoustic impedance phase.

The new wideband acoustic immittance measurement apparatus may provide characterization of the middle ear of a human based on the determined complex acoustic impedance Z(f), e.g. based on the resistance R(f) and the reactance X(f) of the acoustic impedance Z(f); or, based on the acoustic impedance magnitude |Z(f)| and acoustic impedance phase θ(f).

The new wideband acoustic immittance measurement apparatus for determination of wideband acoustic immittance F(f) in the ear of the human, comprises
a processor that is adapted for
  providing an output audio signal to the loudspeaker for conversion into sound for transmission towards a tympanic membrane of the ear and spanning a frequency range, and
  receiving the input audio signal generated by the microphone,
  determining wideband acoustic immittance F(f) as a function of frequency f based on the output audio signal and the input audio signal,
  identifying a middle ear resonance based on the determined wideband acoustic immittance F(f) at a resonance frequency $f_{res}$ at which an acoustic admittance Y(f) = G(f) + jB(f) corresponding to, or calculated from, the determined wideband acoustic immittance F(f) fulfils that the conductance $G(f_{res})$ is a global or local maximum of the conductance G(f) and that the gradient $B'(f_{res})$ of the susceptance B(f) is a global or local minimum of the gradient B'(f).

Throughout the present disclosure, the term "maximum" means a global maximum or a local maximum, and the term "minimum" means a global minimum or a local minimum.

Preferably, the determined wideband acoustic immittance F(f) is the acoustic admittance Y(f). The criteria for identification of a middle ear resonance are based on the realisation that middle ear resonances have characteristics similar to corresponding characteristics of the resonance of a Helmholtz resonator, or network of Helmholtz resonators.

At the resonance frequency $f_0$ of a single Helmholtz resonator, the Helmholtz resonator conductance $G_H(f_0)$ is a global maximum of the Helmholtz resonator conductance $G_H(f)$ as a function of frequency; and the Helmholtz resonator gradient $B_H'(f_0)$ is a global minimum of the gradient of the Helmholtz resonator susceptance $B_H(f)$ as a function of frequency. Thus, corresponding criteria has been established for identification of a middle ear resonance.

Equivalently, at the resonance frequency $f_0$ of a single Helmholtz resonator, the Helmholtz resonator acoustic admittance magnitude $|Y_H(f_0)|$ is a global maximum of the Helmholtz resonator admittance magnitude $|Y_H(f)|$ as a function of frequency; and the Helmholtz resonator phase gradient $\phi_H'(f_0)$ is a global minimum of the Helmholtz resonator phase gradient $\phi_H'(f)$ as a function of frequency. Thus, corresponding criteria has been established for identification of a middle ear resonance.

The immittance F(f) may be represented by the real and imaginary part of the immittance F(f); or, equivalently by the acoustic immittance magnitude and acoustic immittance phase; and other equivalent representations of the acoustic immittance $F(f)$ may be conceived with corresponding equivalent identification criteria for identification of a middle ear resonance.

The determined wideband acoustic immittance $F(f)$ may be another acoustic immittance than the acoustic admittance $Y(f)$, such as the acoustic impedance $Z(f)$, the acoustic reflectance $\Gamma(f)$, the acoustic energy reflectance ER $(f)$, the acoustic absorbance $A(f)$, or any other function that can be determined based on the output audio signal and the input audio signal, and criteria for identification of a middle ear resonance corresponding to, or calculated from, the criteria for the acoustic admittance $Y(f)$ may be established based on the relations between the different acoustic immittances, e.g. see equations (5)-(9) above, and/or based on a comparison of the determined wideband acoustic immittance $F(f)$ with the corresponding wideband acoustic immittance $F_H(f)$ of a Helmholtz resonator, or network of Helmholtz resonators, for identifying one or more middle ear resonances, if any, based on the wideband acoustic immittance $F(f)$, each of which has characteristics of the wideband acoustic immittance $F(f)$ similar to the characteristics of the corresponding wideband acoustic immittance $F_H(f)$ of the Helmholtz resonator, or network of Helmholtz resonators, at the resonance of the Helmholtz resonator, or network of Helmholtz resonators.

The processor may be adapted for identifying a middle ear resonance based on the determined wideband acoustic immittance $F(f)$ at a resonance frequency $f_{res}$ at which an acoustic admittance $Y(f)=G(f)+jB(f)$ corresponding to, or calculated from, the determined wideband acoustic immittance $F(f)$ fulfils either that the conductance $G(f_{res})$ is a global or local maximum of the conductance $G(f)$ or that the gradient $B'(f_{res})$ of the susceptance $B(f)$ is a global or local minimum of the gradient $B'(f)$ and/or based on a comparison of one part of the determined wideband acoustic immittance $F(f)$, e.g. a real part or a magnitude part or an imaginary part or a phase part or a gradient of one of the parts, etc., with the corresponding part of the wideband acoustic immittance $F_H(f)$ of a Helmholtz resonator, or network of Helmholtz resonators, for identifying one or more middle ear resonances, if any, based on the wideband acoustic immittance $F(f)$, each of which has characteristics of the wideband acoustic immittance $F(f)$ similar to the characteristics of the corresponding wideband acoustic immittance $F_H(f)$ of the Helmholtz resonator, or network of Helmholtz resonators, at the resonance of the Helmholtz resonator, or network of Helmholtz resonators.

The resonance frequency $f_{res}$ of a middle ear resonance may be determined with some tolerance.

In the following example, the determined wideband acoustic immittance $F(f)$ is the acoustic admittance $Y(f)$. However, corresponding determinations of a first frequency $f_{res,1}$ and a second frequency $f_{res,2}$ may of course be performed for other determined wideband acoustic immittances $F(f)$, such as the acoustic impedance $Z(f)$, the acoustic reflectance $\Gamma(f)$, the acoustic energy reflectance ER$(f)$, the acoustic absorbance $A(f)$, or any other function that can be determined based on the output audio signal and the input audio signal, and criteria for identification of a middle ear resonance corresponding to, or calculated from, the criteria for the acoustic admittance $Y(f)$ may be established based on the relations between the different acoustic immittances, e.g. see equations (5)-(9) above Thus, the processor may be adapted for identifying a resonance of one or more middle ear resonances, if any, by determining a first frequency $f_{res,1}$ of a maximum, i.e. a local or a global maximum, of, e.g., the conductance $G(f)$ of the determined acoustic admittance $Y(f)$ as a function of frequency f.

The processor may be adapted for identifying the local or global maximum at the first frequency $f_{res,1}$ as a middle ear resonance, and $f_{res,1}$ as the resonance frequency of the middle ear resonance.

Additionally or alternatively, the processor may be adapted for identifying a resonance of one or more middle ear resonances, if any, by determining a second frequency $f_{res,2}$ of a local or global minimum of a gradient of, e.g., the susceptance $B(f)$ of the complex acoustic admittance $Y(f)$ as a function of frequency f, and $f_{res,2}$ as the resonance frequency of the middle ear resonance.

Further, the processor may be adapted for identifying a resonance of one or more middle ear resonances, by comparing the first frequency $f_{res,1}$ with the second frequency $f_{res,2}$, and only if the frequencies $f_{res,1}$ and $f_{res,2}$ are identical, or identical apart from measurement inaccuracies and, optionally, some margin, identifying the local or global maximum as a middle ear resonance, i.e. identifying the local or global maximum as a middle ear resonance only when the distance between the first frequency $f_{res,1}$ and the second frequency $f_{res,2}$ is f less than a threshold value, such as 10%, such as 5%, such as 2%, of the first $f_{res,1}$ or second frequency $f_{res,2}$.

It is an important advantage of the new wideband acoustic immittance measurement apparatus that an air tight seal of the ear canal need not be provided with the ear probe since the determination of the wideband acoustic immittance $F(f)$, e.g. the acoustic admittance $Y(f)$, can take place at ambient pressure. Provision of an air tight seal of the ear canal is cumbersome and time consuming and often the air tight seal is not established in a first attempt. This makes the determination of the wideband acoustic immittance $F(f)$ with the new wideband acoustic immittance measurement apparatus particularly useful for children that often have difficulties avoiding head movements during the determination of wideband acoustic immittance $F(f)$.

Also, no baseline compensation is required for the above-mentioned identification of the middle ear resonance.

The new wideband acoustic immittance measurement apparatus may also determine the wideband acoustic immittance $F(f, p)$, e.g. acoustic admittance $Y(f, p)$, when a static pressure p different from ambient pressure $p_{amb}$ is applied to the ear canal, for identification of one or more middle ear resonances, if any.

Throughout the present disclosure, a mentioning of a wideband acoustic immittance $F(f)$ without the static pressure p means that the immittance $F(f)$ in question; e.g. the acoustic admittance $Y(f)$, acoustic impedance $Z(f)$, acoustic reflectance $\Gamma(f)$, acoustic energy reflectance ER$(f)$, acoustic energy absorbance EA$(f)$, or any other function that can be determined based on the output audio signal and the input audio signal, has been determined at ambient pressure $p_{amb}$.

Thus, the wideband acoustic immittance measurement apparatus may comprise a housing for accommodation of an air pump or compressor for provision of a static pressure p, and the ear probe may have a static pressure output port and an air conduit connected to the static pressure output port, and the cable interconnecting the housing of the apparatus with the ear probe may comprise an air conduit for interconnection of the air conduit of the ear probe with the air pump or compressor for applying the static pressure p to the ear canal with the ear probe forming an air tight seal with the ear canal wall so that the static pressure p in the ear canal can be controlled utilizing the air pump or compressor.

The processor may further be adapted for performing wide band acoustic immittance measurements by controlling the air pump to provide static pressures p spanning a static pressure range, and determining the wideband acoustic immittance F(f, p) as a function of frequency f and static pressure p based on the output audio signal and the input audio signal and the provided static pressure p, such as the complex acoustic admittance Y(f, p), the complex acoustic impedance Z(f, p), the complex acoustic reflectance Γ(f, p), the complex acoustic energy reflectance ER(f, p), the complex acoustic energy absorbance EA(f, p), or any other function that can be determined based on the output audio signal and the input audio signal and the static pressure p.

The processor may be adapted for identifying a middle ear resonance based on the determined wideband acoustic immittance F(f, p) at a resonance frequency $f_{res}$ at which an acoustic admittance Y(f, p)=G(f, p)+jB(f, p) corresponding to, or calculated from, the determined wideband acoustic immittance F(f, p) fulfils that the conductance $G(f_{res}, p)$ is a global or local maximum of the conductance G(f, p) and that the gradient $B'(f_{res}, p)$ of the susceptance B(f, p) is a global or local minimum of the gradient B'(f, p).

The criteria for identification of a middle ear resonance are based on the realisation that middle ear resonances have characteristics that are similar to the characteristics of the resonance of a Helmholtz resonator, or network of Helmholtz resonators.

At the resonance frequency $f_0$ of a single Helmholtz resonator, the Helmholtz resonator conductance $G_H(f_0)$ is a global maximum of the Helmholtz resonator conductance $G_H(f)$ as a function of frequency; and the Helmholtz resonator gradient $B_H'(f_0)$ is a global minimum of the gradient of the Helmholtz resonator susceptance $B_H(f)$ as a function of frequency. Thus, corresponding criteria has been established for identification of a middle ear resonance.

Equivalently, at the resonance frequency $f_0$ of a single Helmholtz resonator, the Helmholtz resonator acoustic admittance magnitude $|Y_H(f_0)|$ is a global maximum of the Helmholtz resonator admittance magnitude $|Y_H(f)|$ as a function of frequency; and the Helmholtz resonator phase gradient $\phi_H'(f_0)$ is a global minimum of the Helmholtz resonator phase gradient $\phi_H'(f)$ as a function of frequency. Thus, corresponding criteria has been established for identification of a middle ear resonance.

The immittance may represented by the real and imaginary part of the immittance; or, equivalently by the acoustic immittance magnitude and acoustic immittance phase; and other equivalent representations of the acoustic immittance may be conceived with corresponding equivalent identification criteria for identification of a middle ear resonance.

Preferably, the determined wideband acoustic immittance F(f, p) is the acoustic admittance Y(f, p); however, the determined wideband acoustic immittance F(f, p) may be another immittance than the acoustic admittance Y(f, p), such as the acoustic impedance Z(f, p), the acoustic reflectance Γ(f, p), the acoustic energy reflectance ER(f, p), the acoustic absorbance A(f, p), or any other function that can be determined based on the output audio signal and the input audio signal, and criteria for identification of a middle ear resonance corresponding to, or calculated from, the criteria for the acoustic admittance Y(f, p) may be established based on the relations between the different acoustic immittances, e.g. see equations (5)-(9) above, and/or based on a comparison of the determined wideband acoustic immittance F(f, p) with the corresponding wideband acoustic immittance $F_H(f)$ of a Helmholtz resonator, or network of Helmholtz resonators, for identifying one or more middle ear resonances, if any, based on the wideband acoustic immittance F(f, p), each of which has characteristics of the wideband acoustic immittance F(f, p) similar to the characteristics of the corresponding wideband acoustic immittance $F_H(f)$ of the Helmholtz resonator, or network of Helmholtz resonators, at the resonance of the Helmholtz resonator, or network of Helmholtz resonators.

The processor may be adapted for identifying one or more middle ear resonances, if any, based on the determined wideband acoustic immittance F(f, p) at a resonance frequency $f_{res}$ at which an acoustic admittance Y(f, p)=G(f, p)+jB(f, p) corresponding to, or calculated from, the determined wideband acoustic immittance F(f, p) fulfils either that the conductance $G(f_{res})$ is a global or local maximum of the conductance G(f, p) or that the gradient $B'(f_{res})$ of the susceptance B(f, p) is a global or local minimum of the gradient B'(f, p).

Alternatively, or additionally, the processor may be adapted for identifying one or more middle ear resonances, if any, based on a comparison of one part of the determined wideband acoustic immittance F(f, p), e.g. a real part or a magnitude part or an imaginary part or a phase part or a gradient of one of the parts, etc., with the corresponding part of the wideband acoustic immittance $F_H(f)$ determined for a Helmholtz resonator, or network of Helmholtz resonators, for identifying one or more middle ear resonances, if any, at respective resonance frequencies $f_{res}$ at which the wideband acoustic immittance $F(f_{res}, p)$ has characteristics similar to the characteristics of the corresponding wideband acoustic immittance $F_H(f)$ of the Helmholtz resonator, or network of Helmholtz resonators, at the resonance frequency $f_0$ of the Helmholtz resonator, or at a resonance $f_0$ of the network of Helmholtz resonators.

The resonance frequency $f_{res}$ of a middle ear resonance may be determined with some tolerance.

In the following example, the determined wideband acoustic immittance F(f, p) is the acoustic admittance Y(f, p). However, corresponding determinations of a first frequency $f_{res,1}$ and a second frequency $f_{res,2}$ may of course be performed for other determined wideband acoustic immittances F(f, p), such as the acoustic impedance Z(f, p), the acoustic reflectance Γ(f, p), the acoustic energy reflectance ER(f, p), the acoustic absorbance A(f, p), or any other function that can be determined based on the output audio signal and the input audio signal, and criteria for identification of a middle ear resonance corresponding to, or calculated from, the criteria for the acoustic admittance Y(f, p) may be established based on the relations between the different acoustic immittances, e.g. see equations (5)-(9) above Thus, the processor may be adapted for identifying a resonance of one or more middle ear resonances, if any, by determining a first frequency $f_{res,1}$ of a maximum, i.e. a local or a global maximum, of, e.g., the conductance G(f, p) of the determined acoustic admittance Y(f, p) as a function of frequency f.

The processor may be adapted for identifying the local or global maximum at the first frequency $f_{res,1}$ as a middle ear resonance, and $f_{res,1}$ as the resonance frequency of the middle ear resonance.

Additionally or alternatively, the processor may be adapted for identifying a resonance of one or more middle ear resonances, if any, by determining a second frequency $f_{res,2}$ of a local or global minimum of a gradient of, e.g., the susceptance B(f, p) of the complex acoustic admittance Y(f, p) as a function of frequency f, and $f_{res,2}$ as the resonance frequency of the middle ear resonance.

Further, the processor may be adapted for identifying a resonance of one or more middle ear resonances, by comparing the first frequency $f_{res,1}$ with the second frequency $f_{res,2}$, and only if the frequencies $f_{res,1}$ and $f_{res,2}$ are identical, or identical apart from measurement inaccuracies and, optionally, some margin, identifying the local or global maximum as a middle ear resonance, i.e. identifying the local or global maximum as a middle ear resonance only when the distance between the first frequency $f_{res,1}$ and the second frequency $f_{res,2}$ is f less than a threshold value, such as 10%, such as 5%, such as 2%, of the first $f_{res,1}$ or second frequency $f_{res,2}$.

The processor may be adapted for performing the determination of wideband acoustic immittance F(f, p) applying static pressures p through the ear probe, such as static pressures of 0 daPa, TPP, 200 daPa, −400 daPa, etc.

The determination of the wideband acoustic immittance F(f), e.g. the acoustic admittance Y(f), of the ear includes the acoustic immittance $F_{EC}(f)$ of the ear canal, e.g. the acoustic admittance $Y_{EC}(f)$ of the ear canal. The ear canal is however redundant to the characteristics of the middle and inner ear and therefore it may be desirable to eliminate or reduce the contribution of the ear canal from the determined wideband acoustic immittance F(f), e.g. acoustic admittance Y(f), before identification of one or more middle ear resonances, if any.

In conventional tympanometry, it is recognized that the determination the acoustic admittance Y(f), of the ear includes the acoustic admittance $Y_{EC}(f)$ of the ear canal. The ear canal is however redundant to the characteristics of the middle and inner ear and therefore it may be desirable to eliminate or reduce the contribution $Y_{EC}(f)$ of the ear canal before identification of a middle ear resonance.

In conventional tympanometry, the contribution $Y_{EC}(f)$ of the ear canal is reduced by subtracting the acoustic admittance $Y_{EC}(f, p_{ref})$ measured with a high or low static pressure $p_{ref}$ of, e.g. $p_{ref1}$=200 daPa or $p_{ref2}$=−400 daPa, applied to the ear canal through the ear probe. A high or low static pressure inside the ear canal causes the tympanic membrane to tension and become hard like a wall so that the contribution of the ear canal to the acoustic admittance of the ear is believed to be eliminated or reduced by forming the baseline compensated acoustic admittance:

$$Y_{BC}(f,p_{ref})=Y(f)-Y_{EC}(f,p_{ref}).$$

In conventional tympanometry, a primary middle ear resonance frequency is identified based on the baseline compensated acoustic admittance at the frequency at which the baseline compensated susceptance $B_{BC}(f, p_{ref})$ is equal to 0 mmho.

This may not be accurate and may lead to erroneous identification of middle ear resonances.

Further, the new wideband acoustic immittance measurement apparatus is configured for identifying middle ear resonances based on baseline compensation in a new and accurate way as further explained below, so that the inaccuracy of known baseline compensation has been eliminated or reduced.

The processor may be adapted for performing baseline compensation, e.g. the processor may be adapted for determining a baseline compensated acoustic admittance $Y_{BC}(f, p_1, p_2)=Y_1(f, p_1)-Y_2(f, p_2)$ between a determined acoustic admittance $Y_1(f, p_1)$ as a function of frequency f at a first static pressure $p_1$ and a determined acoustic admittance $Y_2(f, p_2)$ as a function of frequency f at a second static pressure $p_2$, and identifying a middle ear resonance, if any, based on the baseline compensated acoustic admittance $Y_{BC}(f, p_1, p_2)$ by determining a first frequency $f_{res,1}$ and a second frequency $f_{res,2}$ at which the baseline compensated acoustic admittance $Y_{BC}(f, p_1, p_2)=Y_1(f, p_1)-Y_2(f, p_2)$ fulfils that the baseline compensated conductance $G_{BC}(f_{res,1}, p_1, p_2)=G_1(f_{res,1}, p_1)-G_2(f_{res,1}, p_2)$ of the baseline compensated acoustic admittance $Y_{BC}(f, p_1, p_2)$ is a local or global maximum and that the gradient $B'(f_{res,2}, p_1, p_2)$ of the baseline compensated acoustic susceptance $B_{BC}(f, p_1, p_2)=B_1(f, p_1)-B_2(f, p_2)$ is a local or global minimum and identifying a middle ear resonance when the absolute value of the difference between fres,1 and fres,2 is less than a threshold value determined by measurement inaccuracies and, optionally, some margin, such as 10%, such as 5%, such as 2%, of the first $f_{res,1}$ or second frequency $f_{res,2}$.

Corresponding baseline compensations may be performed for another immittance, such as the acoustic impedance Z(f), the acoustic reflectance Γ(f), the acoustic energy reflectance ER (f), the acoustic absorbance A(f), etc.

For example, a corresponding baseline compensated acoustic impedance $Z_{BC}(f, p_1, p_2)$ is given by:

$$Z_{BC}(f, p_1, p_2) = \frac{Z_1(f, p_1) * Z_2(f, p_2)}{Z_2(f, p_2) - Z_1(f, p_1)}.$$

The first static pressure $p_1$ may be the ambient pressure $p_{amb}$; or, the first static pressure $p_1$ may be the tympanic peak pressure TPP, etc.

The second static pressure $p_2$ may be 200 daPa; or, the second static pressure $p_2$ may be −400 daPa, etc.

The frequency range of the output audio signal, and thereby the emitted sound, may include the frequency range from 200 Hz-3 kHz.

The frequency range of the output audio signal, and thereby the emitted sound, may include the frequency range from 200 Hz-4 kHz.

The processor may be adapted for controlling a display, e.g. a printer, a display screen, etc., to show a plot of the determined acoustic immittance F (f) and/or F (f, p) and/or $F_{BC}(f, p_1, p_2)$ with one or more identifications of corresponding one or more middle ear resonances.

Advantageously, the new wideband acoustic immittance measurement apparatus is not dependent on accurate calibration.

The new wideband acoustic immittance measurement apparatus may be a self-contained unit with its own user interface with switches and a display, possibly a keyboard, as is well-known in the art of immittance measurement apparatuses.

The new wideband acoustic immittance measurement apparatus may also be based on a general purpose computer, such as a PC, laptop, PDA, smartphone, etc., for recording to the test results and that comprises the user interface of the wideband acoustic immittance measurement apparatus and that is interconnected with and controls a special purpose apparatus with the required measurement circuitry and devices for performing the determination of wideband acoustic immittance F(f, p) in the ear of the human.

The recorded test results may be stored together with the identification of the right ear or the left ear that the stored test results relate to in the wideband acoustic immittance measurement apparatus and possibly other relevant information, such as the date, time, patient ID, operator ID, etc.

The recorded data may be transferred to another device, such as a remote storage, such as a server interconnected with the wideband acoustic immittance measurement apparatus through a Wide Area Network, such as the Internet.

The ear probe may be connected with a cable to the wideband acoustic immittance measurement apparatus in a well-known way.

The cable may include electrical conductors for interconnection of a microphone and a loudspeaker and switches and possible indicators, respectively, accommodated in the probe housing.

The cable may also have an air conduit for interconnection with a pump in the wideband acoustic immittance measurement apparatus for control of the static pressure in the ear canal subjected to clinical testing or screening in a way well-known in the art of acoustic immittance measurements.

The ear probe preferably comprises a conventional ear probe tip that is preferably configured for fitting with an ear tip for insertion into an ear canal of the patient and for sealing the ear canal with an air tight seal.

The ear probe tip may provide an output of an air conduit connected with the air conduit of the cable to the wideband acoustic immittance measurement apparatus.

The ear tip may be disposable and for example made of rubber.

The results of the ear measurements performed with the wideband acoustic immittance measurement apparatus and the ear probe are recorded by the wideband acoustic immittance measurement apparatus and stored in a memory of the wideband acoustic immittance measurement apparatus. The results are stored together with an indication of whether the right ear or the left ear was subject to the testing as selected with the user interface.

BRIEF DESCRIPTION OF THE DRAWINGS

In order to enhance their clarity and improve understanding of the various elements and embodiments of the invention, elements in the figures have not necessarily been drawn to scale. Furthermore, elements that are known to be common and well understood to those in the industry are not depicted in order to provide a clear view of the various embodiments of the invention, thus the drawings are generalized in form in the interest of clarity and conciseness.

DETAILED DESCRIPTION OF THE INVENTION

In the following discussion that addresses a number of embodiments and applications of the present invention, reference is made to the accompanying drawings that form a part hereof, and in which is shown by way of illustration specific embodiments in which the invention may be practiced. It is to be understood that other embodiments may be utilized, and changes may be made without departing from the scope of the present invention.

Various illustrative examples of the new wideband acoustic immittance measurement apparatus according to the appended claims will now be described more fully hereinafter with reference to the accompanying drawings, in which various embodiments of the new wideband acoustic immittance measurement apparatus are illustrated. The new wideband acoustic immittance measurement apparatus according to the appended claims may, however, be embodied in different forms and should not be construed as limited to the embodiments set forth herein. In addition, an illustrated embodiment needs not have all the aspects or advantages shown. An aspect or an advantage described in conjunction with a particular embodiment is not necessarily limited to that embodiment and can be practiced in any other examples even if not so illustrated, or if not so explicitly described.

It should also be noted that the accompanying drawings are schematic and simplified for clarity, and they merely show details which are essential to the understanding of the new wideband acoustic immittance measurement apparatus, while other details have been left out.

As used herein, the singular forms "a," "an," and "the" refer to one or more than one, unless the context clearly dictates otherwise.

Figure 1:
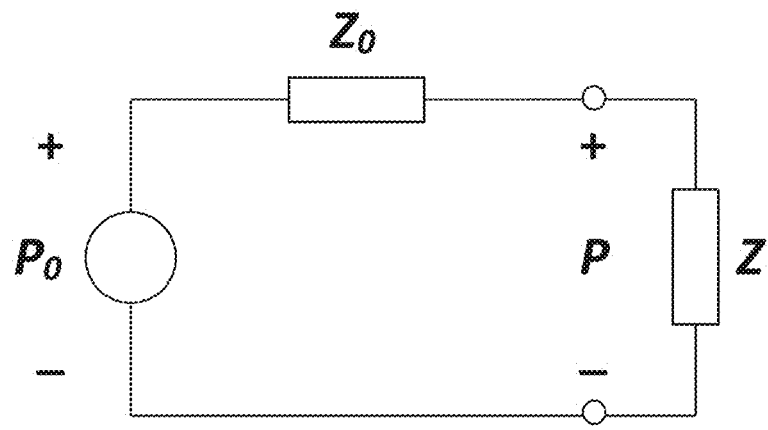
FIG. 1 shows a circuit diagram of a Thévenin equivalent circuit for an immittance measurement performed with an ear probe.
Figure 2:
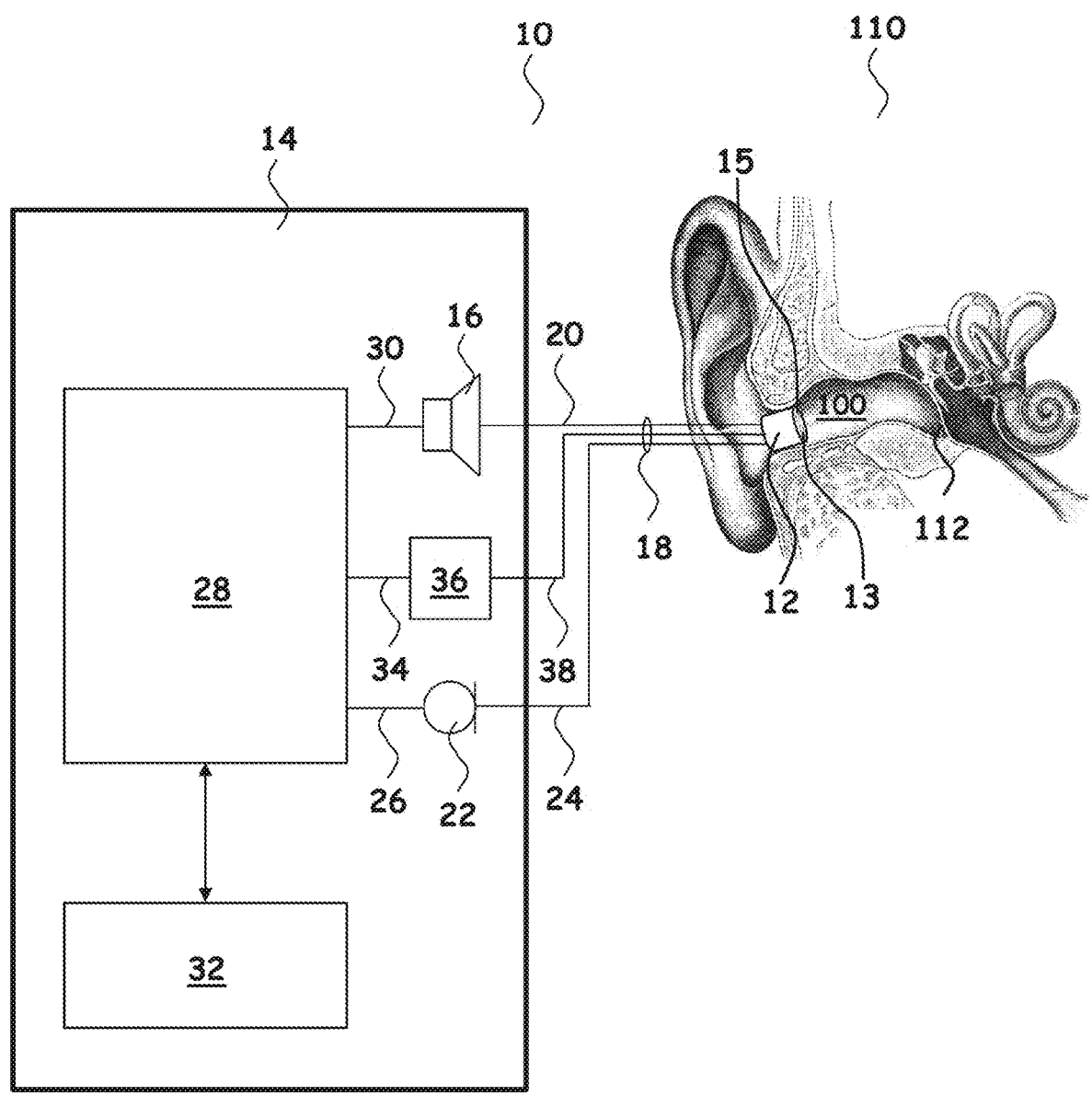
FIG. 2 schematically illustrates the new wideband acoustic immittance measurement apparatus.

FIG. 2 schematically illustrates one example of the new wideband acoustic immittance measurement apparatus 10 with the ear probe 12 positioned with its acoustic output port at or inside an ear canal 100 of an ear 110 of a human.

The ear probe 12 of the illustrated wideband acoustic immittance measurement apparatus 10 has an acoustic output port (not visible) for emission of sound towards the tympanic membrane 112 of the ear 110 and an acoustic input port (not visible) for reception of sound in the ear 110.

A housing 14 of the wideband acoustic immittance measurement apparatus 10 accommodates a loudspeaker 16 for emission of the sound. A cable 18 interconnects the housing 14 with the ear probe 12 and has an air conduit 20 for transmission of the acoustic sound from the loud speaker 16 in the housing 14 to the acoustic output port (not visible) of the ear probe 12.

The housing 14 further accommodates a microphone 22 for generation of an input audio signal 26 as a function of sound received at the acoustic input port of the ear probe 12. The cable 18 has an air conduit 24 for transmission of the sound received at the acoustic input port of the ear probe 12 to the microphone 22 for conversion into the corresponding input audio signal 26.

The housing 14 further accommodates a processor 28 that is adapted for controlling the loudspeaker 16 to emit sound spanning a frequency range by generation of an output audio signal 30 that is input to the loudspeaker 16 for conversion into the corresponding emitted sound transmitted through the air conduit 20 of the cable 18 and through the acoustic output port (not visible) of the ear probe 12 and into the ear canal 100 for propagation towards the tympanic membrane 112 at the end of the ear canal 100.

The processor 28 is also connected to the output of the microphone 22 for reception of the input audio signal 26 generated by the microphone 22 in response to sound received at the input port of the ear probe 12.

In the wideband acoustic immittance measurement apparatus 10 shown in FIG. 2, the housing 14 accommodates both of the loudspeaker 16 and the microphone 22. Other wideband acoustic immittance measurement apparatuses according to the appended set of claims are provided wherein the ear probe 12 accommodates the loudspeaker 16 and the microphone 22, and wherein the air conduits 20, 24 are substituted with electrical conductors for electrical connection of the input audio signal 26 and the output audio signal 30, respectively, with the microphone and the loudspeaker in the ear probe.

Yet other wideband acoustic immittance measurement apparatuses according to the appended set of claims are provided wherein the ear probe accommodates one of the loudspeaker 16 and the microphone 22, and wherein the corresponding air conduit 20, 24 is substituted with an electrical conductor for connection of the respective one of the input audio signal 26 and the output audio signal 30 to the one of the loudspeaker 16 and the microphone 22.

Optionally, the illustrated wideband acoustic immittance measurement apparatus 10 has an air pump or compressor 36 accommodated in the housing 14 for provision of a static pressure p in the ear canal 100. The processor 28 is adapted for controlling the static pressure p provided by the air pump or compressor 36 with control signal 34. The static pressure p is applied to the ear canal through an air conduit 38 of the cable 18 and through an air conduit (not visible) through the ear probe 12. The ear probe 12 seals the ear canal 100 with an air tight seal so that the static pressure p in the ear canal 100 can be adjusted with the air pump or compressor 36 as controlled by the processor 28.

The processor 28 is adapted for determining a wideband acoustic immittance F(f, p) of the ear 110 based on the audio output signal 30 and the input audio signal 26, optionally at one or more static pressures p.

The processor 28 is adapted for identifying a middle ear resonance by comparing characteristics of the determined immittance F(f, p) with the characteristics of a resonance of a Helmholtz resonator, or a network of Helmholtz resonators, of a corresponding immittance $F_H(f)$ of the Helmholtz resonator, or network of Helmholtz resonators.

The determined wideband acoustic immittance F(f, p) may be any function that can be determined based on measurement with the ear probe, i.e. based on the output audio signal 30 and the input audio signal 26, including the previously mentioned acoustic immittances F(f, p), namely acoustic admittance Y(f, p), acoustic impedance Z(f, p), acoustic reflectance Γ(f, p), acoustic energy reflectance ER(f, p), and acoustic energy absorbance EA(f, p), including any function that can be determined based on measurement with the ear probe at ambient pressure $p_{amb}$, i.e. based on the output audio signal 30 and the input audio signal 26 at ambient pressure $p_{amb}$, including acoustic admittance Y(f), acoustic impedance Z(f), acoustic reflectance Γ(f), acoustic energy reflectance ER(f), and acoustic energy absorbance EA(f).

Throughout the present disclosure, wideband acoustic immittance determined at ambient pressure $p_{amb}$ is written F(f) omitting the static pressure p, such as acoustic admittance Y(f), acoustic impedance Z(f), acoustic reflectance Γ(f), acoustic energy reflectance ER(f), and acoustic energy absorbance EA(f).

The processor 28 is further adapted for identifying one or more middle ear resonances, if any, based on the wideband acoustic immittance F(f) determined at ambient pressure $p_{amb}$.

The processor 28 of the wideband acoustic immittance measurement apparatus shown in FIG. 2, is adapted for determining complex acoustic admittance $Y(f)=G(f)+j*B(f)=|Y(f)|\beta e^{j\phi(f)}$ with the ear probe 12 positioned in the ear 110 of the human.

The real part of the acoustic admittance Y(f) is the conductance G(f), and the imaginary part of the acoustic admittance Y(f) is the susceptance B(f).

|Y(f)| is the magnitude of the acoustic admittance Y(f), in short the acoustic admittance magnitude; and φ(f) is the phase of the acoustic admittance Y(f), in short the acoustic admittance phase.

The processor 28 is further adapted for identifying one or more middle ear resonances, if any, based on the determined complex acoustic admittance Y(f), e.g. based on the conductance G(f) and the susceptance B(f) of the acoustic admittance Y(f); or, based on the acoustic admittance magnitude |Y(f)| and acoustic admittance phase φ(f).

Optionally and selectably, the processor 28 is adapted for determining complex acoustic impedance $Z(f)=R(f)+j*X(f)=|Z(f)|e^{j\theta(f)}$ with the ear probe 12 positioned in the ear 110 of the human.

The real part of the acoustic impedance Z(f) is the resistance R(f), and the imaginary part of the acoustic impedance Z(f) is the reactance X(f).

|Z(f)| is the magnitude of the acoustic impedance Z(f), in short the acoustic impedance magnitude, and θ(f) is the phase of the acoustic impedance Z(f), in short the acoustic impedance phase.

Optionally and selectably, the processor 28 is further adapted for identifying one or more middle ear resonances, if any, based on the determined complex acoustic impedance Z(f), e.g. based on the resistance R(f) and the reactance X(f) of the acoustic impedance Z(f); or, based on the acoustic impedance magnitude |Z(f)| and acoustic impedance phase θ(f).

Optionally and selectably, the processor is adapted for determining another immittance F(f), i.e. any function that can be determined based on measurement with the ear probe 12 based on the output audio signal 30 and the input audio signal 26, such as acoustic reflectance Γ(f), acoustic energy reflectance ER(f), and acoustic energy absorbance EA(f).

Optionally and selectably, the processor 28 is further adapted for identifying one or more middle ear resonances, if any, based on the determined other immittance F(f).

At its resonance frequency $f_0$ of a single Helmholtz resonator, the Helmholtz resonator conductance $G_H(f_0)$ is a global maximum of the Helmholtz resonator conductance $G_H(f)$ as a function of frequency; and the Helmholtz resonator gradient $B_H'(f_0)$ is a global minimum of the gradient of the Helmholtz resonator susceptance $B_H(f)$ as a function of frequency.

The processor 28 is adapted for identifying a possible middle ear resonance of a possible plurality of middle ear resonances by determining a possible first frequency $f_{res,1}$ of a local or global maximum $G(f_{res,1})$ of the conductance G(f) of the complex acoustic admittance Y(f) as a function of frequency f.

Further, the processor 28 is adapted for determining a possible second frequency $f_{res,2}$ of a local or global minimum of a gradient of the susceptance B(f) of the complex acoustic admittance Y(f) as a function of frequency f.

The processor 28 is adapted for identifying the possible middle ear resonance of one or more middle ear resonances, by comparing the first frequency $f_{res,1}$ with the second frequency $f_{res,2}$, and if the frequencies are identical, or identical apart from measurement inaccuracies and, optionally, some margin, identifying the local or global maximum as a middle ear resonance, e.g. identifying the local or global maximum of the conductance $G(f_{res,1})$ as a middle ear resonance when the distance between the first frequency $f_{res,1}$ and the second frequency $f_{res,2}$ is f less than a threshold value, such as 10%, such as 5%, such as 2%, of the first frequency $f_{res,1}$ or the second frequency $f_{res,2}$.

Optionally and selectably, the processor 28 is adapted for identifying the local or global maximum $G(f_{res,1})$ of the conductance $G(f)$ at the first frequency $f_{res,1}$ as a middle ear resonance without the comparison.

Optionally and selectably, the processor 28 is adapted for identifying the local or global minimum $B'(f_{res,2})$ of the gradient $B'(f)$ of the susceptance $B(f)$ at the second frequency $f_{res,2}$ as a middle ear resonance without the comparison.

Equivalently, at the resonance frequency $f_0$ of a single Helmholtz resonator, the Helmholtz resonator acoustic admittance magnitude $|Y_H(f_0)|$ is a global maximum of the Helmholtz resonator admittance magnitude $|Y_H(f)|$ as a function of frequency; and the Helmholtz resonator phase gradient $\phi_H'(f_0)$ is a global minimum of the Helmholtz resonator phase gradient $\phi_H'(f)$ as a function of frequency. Thus, corresponding criteria has been established for identification of a middle ear resonance.

Optionally and selectably, the processor 28 is adapted for identifying a possible middle ear resonance by determining a first frequency $f_{res,1}$ of a possible local or global maximum $|Y(f_{res,1})|$ of the magnitude $|Y(f)|$ of the complex acoustic admittance $Y(f)$ as a function of frequency f.

The processor 28 is further adapted for determining a second frequency $f_{res,2}$ where the gradient $\phi'(f)$ of the phase $\phi(f)$ of the acoustic admittance $Y(f)$ has a local or global minimum $\phi'(f_{res,2})$.

The processor 28 is adapted for comparing the first frequency $f_{res,1}$ with the second frequency $f_{res,2}$, and if the frequencies are identical, or identical apart from measurement inaccuracies and, optionally, some margin, identifying the local or global maximum of the magnitude $|Y(f)|$ as a middle ear resonance, e.g. identifying the local or global maximum as a middle ear resonance when the distance between the first frequency $f_{res,1}$ and the second frequency $f_{res,2}$ is f less than a threshold value, such as 10%, such as 5%, such as 2%, of the first frequency.

Optionally and selectably, the processor 28 may be adapted for identifying the local or global maximum $|Y(f_{res,1})|$ of the magnitude $|Y(f)|$ at the first frequency $f_{res,1}$ as a middle ear resonance without the comparison.

Optionally and selectably, the processor 28 may be adapted for identifying the local or global minimum $\phi'(f_{res,2})$ of the gradient $\phi'(f)$ of the phase $\phi(f)$ at the second frequency $f_{res,2}$ as a middle ear resonance without the comparison.

Optionally and selectably, the processor 28 may be adapted for identifying a possible middle ear resonance of a possible plurality of middle ear resonances based on another determined wideband acoustic immittance $F(f)$ than the admittance $Y(f)$, by calculating the admittance $Y(f)$ based on the determined wideband acoustic immittance $F(f)$, e.g. in accordance with one of the equations (5)-(9) and identifying the possible middle ear resonance(s) as explained above.

Optionally and selectably, the processor 28 may be adapted for identifying a possible middle ear resonance of a possible plurality of middle ear resonances based on another determined wideband acoustic immittance $F(f)$ than the acoustic admittance $Y(f)$, by calculating criteria for identification of a possible middle ear resonance of a possible plurality of middle ear resonances corresponding to the criteria for the acoustic admittance $Y(f)$ set out above based on the determined wideband acoustic immittance $F(f)$, e.g. in accordance with one of the equations (5)-(9), and identifying the possible middle ear resonance(s) based on the corresponding criteria.

For example, if the determined wideband acoustic immittance $F(f)$ is the acoustic impedance $Z(f)$, the processor 28 may be adapted for calculating the corresponding acoustic admittance $Y(f)$ in accordance with equation (5) and identify possible middle ear resonances for the corresponding acoustic admittance $Y(f)$ as explained above.

Alternatively, or additionally, the processor 28 may be adapted for calculating criteria for the acoustic impedance $Z(f)$ that corresponds to the criteria for identification of a possible middle ear resonance of a possible plurality of middle ear resonances set out above for the acoustic admittance $Y(f)$, i.e. in accordance with equation (5) a local or global maximum of the acoustic conductance $G(f)$ corresponds to a local or global minimum of the acoustic resistance $R(f)$ and a local or global minimum of the gradient of the acoustic susceptance $B(f)$ corresponds to a local or global maximum of the gradient of the acoustic reactance $X(f)$; and a local or global maximum of the magnitude $|Y(f)|$ of the acoustic admittance $Y(f)$ corresponds to a minimum of the magnitude $|R(f)|$ of the acoustic impedance $Z(f)$ and a local or global minimum of the gradient $\phi'(f)$ of the phase $\phi(f)$ of the acoustic admittance $Y(f)$ corresponds to a maximum of the gradient $\theta'(f)$ of the phase $\theta(f)$ of the acoustic impedance $Z(f)$.

The processor 28 is connected to a user interface 32 that includes a display (not shown), and the processor 28 is adapted for controlling the display to show a plot of the determined acoustic admittance $Y(f)$ on the display including markings, e.g. arrows, of determined middle ear resonances of the acoustic admittance $Y(f)$ and/or $Y_{BC}(f)$ and/or $Y(f, p)$.

Optionally and selectably, the processor 28 is adapted for controlling the display to show plot(s) of one or more other immittances $F(f)$, i.e. any function that can be determined based on measurement with the ear probe 12 based on the output audio signal 30 and the input audio signal 26, such as acoustic reflectance $\Gamma(f)$, acoustic energy reflectance $ER(f)$, and acoustic energy absorbance $EA(f)$, including markings, e.g. arrows, of determined middle ear resonances based on the plotted acoustic immittance $F(f)$.

In the illustrated new wideband acoustic immittance measurement apparatus 10, the user interface 32 is accommodated in the housing 14. In another new wideband acoustic immittance measurement apparatus, the wideband acoustic immittance measurement apparatus is controlled by an external computer (not shown), such as a personal computer, a tablet, a smartphone, etc., and the processor 28 is connected to the user interface of the external computer.

Figure 3:
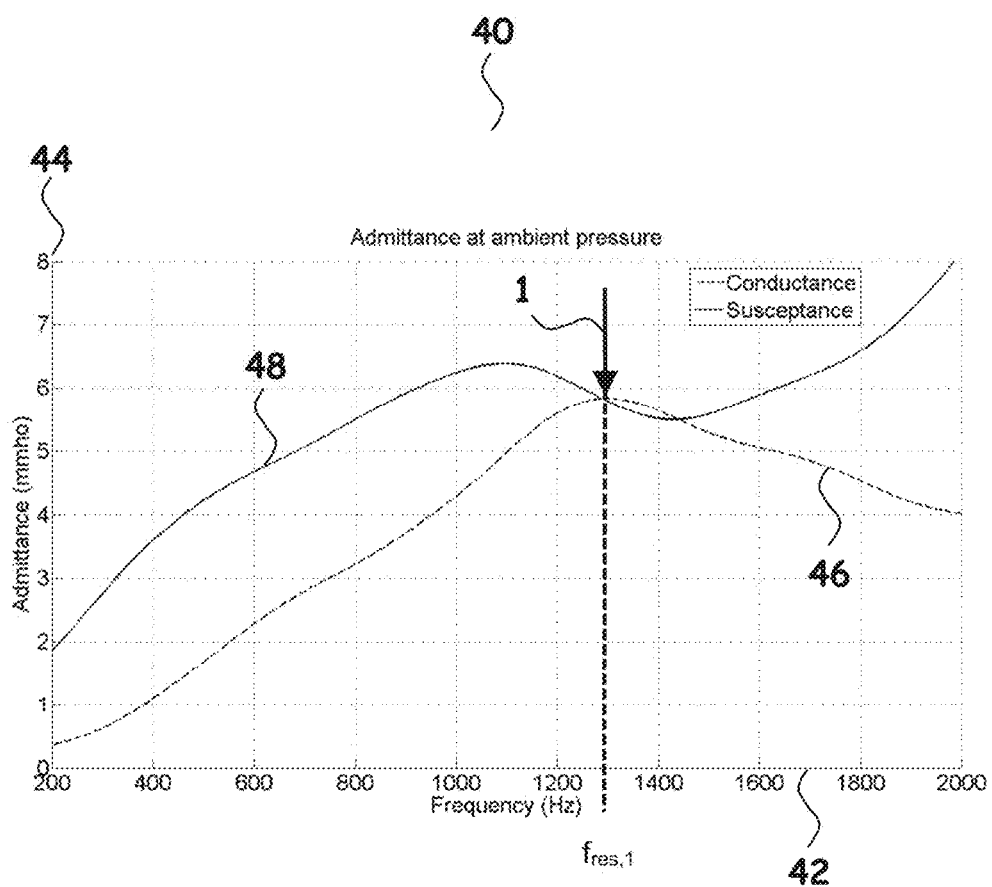
FIG. 3 shows an exemplary output plot generated by the new wideband acoustic immittance measurement apparatus and obtained at ambient pressure.

FIG. 3 shows an exemplary acoustic admittance plot 40 displayed on the display of the new wideband acoustic immittance measurement apparatus 10. In FIG. 3, frequency is plotted along the x-axis 42 and values in mmho of the conductance $G(f)$ and susceptance $B(f)$ are plotted along the y-axis 44. The dashed curve 46 shows a plot of the conductance $G(f)$, and the solid curve 48 shows a plot of the susceptance $B(f)$. The admittance $Y(f)$ was determined at ambient pressure $p_{amb}$.

In the plot 40, one middle ear resonance has been identified and marked by arrow 1 displayed on the display. The first frequency $f_{res,1}$ at which the processor 28 has determined a local or global maximum of the conductance $G(f)$ 46 is also shown. The distance between $f_{res,1}$ and $f_{res,2}$ was less than 10 Hz and is not shown.

Figure 4:
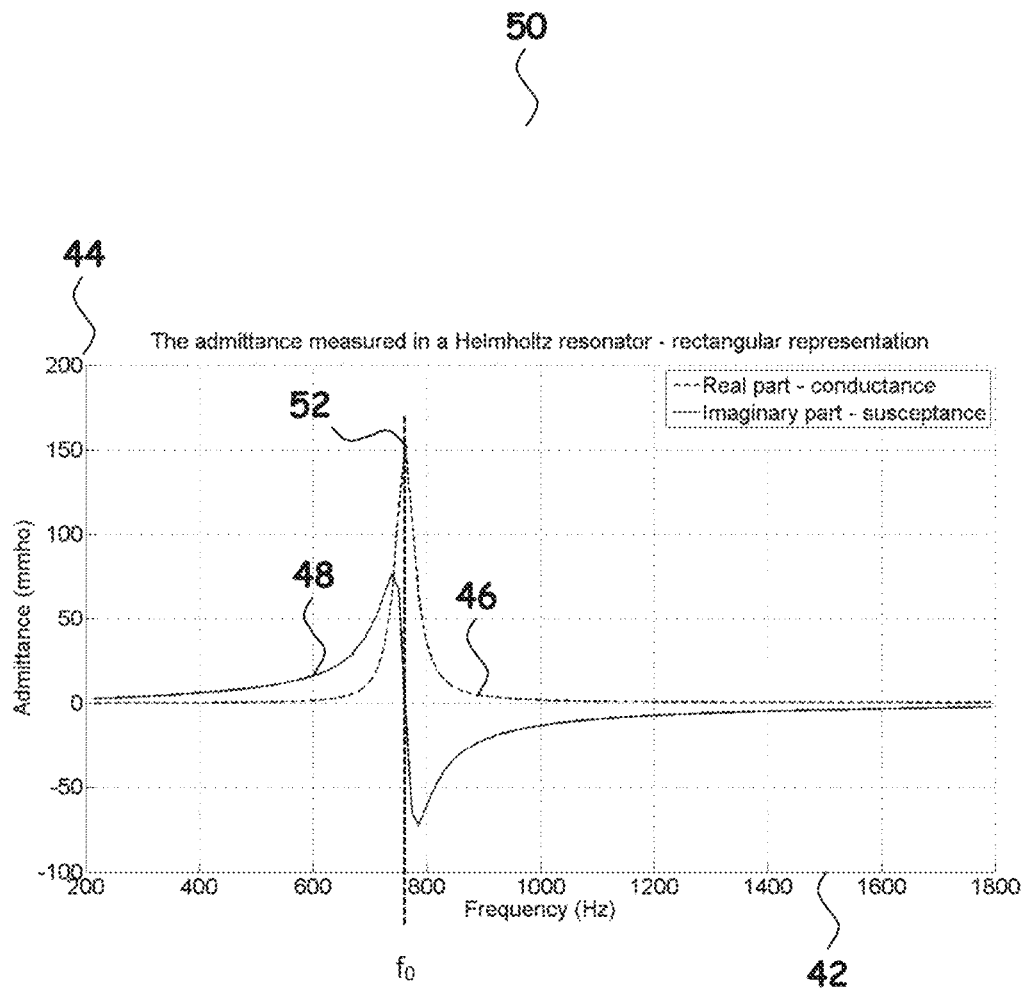
FIG. 4 shows plots of the conductance G(f) and susceptance B(f) of a Helmholtz resonator.
Figure 5:
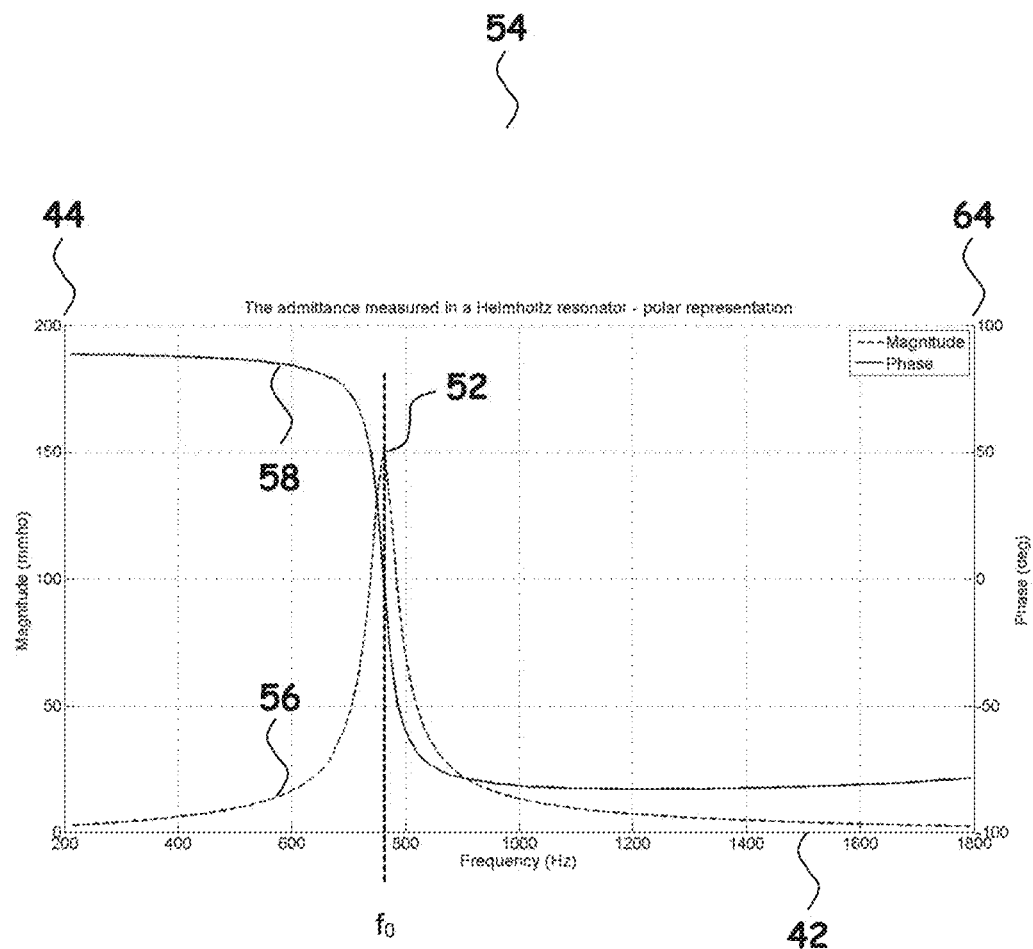
FIG. 5 shows plots of the magnitude $|Y_H(f)|$ and phase $\phi(f)$ of the acoustic admittance $Y_H(f)$ of a Helmholtz resonator.

In order to illustrate the criteria on which the identification of the middle ear resonance of the plot 40 shown in FIG. 3 is based, plots 50, 54 of the acoustic admittance $Y_H$ (f) of a Helmholtz resonator are shown in FIGS. 4 and 5.

In FIG. 4, frequency is plotted along the x-axis 42 and values in mmho of the conductance $G_H$ (f) and susceptance $B_H$ (f) of the Helmholtz resonator is plotted along the y-axis 44. The dashed curve 46 shows a plot of the conductance $G_H$ (f), and the solid curve 48 shows a plot of the susceptance $B_H$ (f).

The plot 50 shows that at resonance 52, the conductance $G_H$ ($f_0$) 46 has a global maximum while the gradient, which has a negative value, of the susceptance $B_H$ ($f_0$) 48 has a global minimum. One of these features, or the combined features of the acoustic admittance Y(f) of the ear of the human may be used to identify one or more middle ear resonances based on the determined acoustic admittance Y(f), e.g., as plotted in FIG. 3, or another wideband acoustic admittance F(f).

In FIG. 5, frequency is plotted along the x-axis 42 and values in mmho of the magnitude $|Y_H (f)|$ is plotted along the y-axis 44 and values in degrees of the phase $\phi_H$ (f) is plotted along the y-axis 64. The dashed curve 56 shows a plot of the magnitude $|Y_H (f)|$, and the solid curve 58 shows a plot of the phase $\phi_H$ (f).

The plot 54 shows that at middle ear resonance 52, the magnitude $|Y_H (f_0)|$ has a global maximum while the (negative) gradient $\phi_H'(f_0)$ of the phase $\phi_H$ (f) has a global minimum. One of these features, or the combined features, of the acoustic admittance Y(f) may be used to identify one or more middle ear resonances of the determined acoustic admittance Y(f) or another wideband acoustic admittance F(f).

It is an important advantage of the new wideband acoustic immittance measurement apparatus 10 that an air tight seal of the ear canal 100 need not be provided with the ear probe 12 since the determination of the acoustic admittance Y(f), or another wideband acoustic admittance F(f), as a function of frequency f can take place at ambient pressure $p_{amb}$.

Provision of an air tight seal of the ear canal 100 is cumbersome and time consuming and often establishment of the air tight seal requires more than one attempt.

This makes the new wideband acoustic immittance measurement apparatus 10 particularly useful for examination of children that often have difficulties avoiding head movements during the measurement.

Also, the new wideband acoustic immittance measurement apparatus 10 requires no baseline compensation for the above-mentioned identification of the one or more middle ear resonances making the identification more simple and accurate.

However, determination of wideband acoustic immittance at different static pressures p and baseline compensation may provide useful information on the ear.

In conventional tympanometry, it is recognized that the determination the acoustic admittance Y(f), of the ear includes the acoustic admittance $Y_{EC}$(f) of the ear canal. The ear canal is however redundant to the characteristics of the middle and inner ear and therefore it may be desirable to eliminate or reduce the contribution $Y_{EC}$(f) of the ear canal before identification of a middle ear resonance.

In conventional tympanometry, the contribution $Y_{EC}$(f) of the ear canal is reduced by subtracting the acoustic admittance $Y_{EC}$(f, $p_{ref}$) measured with a high or low static pressure $p_{ref}$ of, e.g. $p_{ref1}$=200 daPa or $p_{ref2}$=−400 daPa, applied to the ear canal through the ear probe. A high or low static pressure inside the ear canal causes the tympanic membrane to tension and become hard like a wall so that the contribution of the ear canal to the acoustic admittance of the ear is believed to be eliminated or reduced by forming the baseline compensated acoustic admittance:

$$Y_{BC}(f,p_{ref})=Y(f)-Y_{EC}(f,p_{ref}).$$

In conventional tympanometry, a primary middle ear resonance frequency is identified based on the baseline compensated acoustic admittance at the frequency at which the baseline compensated susceptance $B_{BC}(f, p_{ref})$ is equal to 0 mmho.

As mentioned above in connection with FIG. 2, optionally, the wideband acoustic immittance measurement apparatus 10 shown in FIG. 2 is also capable of determining wideband acoustic immittance F (f, p) at static pressures p different from ambient pressure $p_{amb}$.

The following disclosure relates to a wideband acoustic immittance measurement apparatus 10 that does have the air pump or compressor 36 accommodated in the housing 14 as shown in FIG. 2.

Further, the wideband acoustic immittance measurement apparatus 10 disclosed below, is configured for identifying middle ear resonances based on baseline compensation in a new and accurate way.

The processor 28 is further adapted for controlling the air pump or compressor 36 to provide static pressures p spanning a static pressure range including ambient static pressure, e.g. from $p_{ref2}$=−400 daPa below ambient pressure to $p_{ref1}$=200 daPa above ambient pressure, and determining the wideband acoustic immittance F(f, p), e.g. complex acoustic admittance Y(f, p), as a function of frequency f as disclosed above and additionally as a function of static pressure p, based on the input and output audio signals 26, 30 and the provided static pressure p.

Thus, the processor 28 is adapted for performing wide band acoustic immittance measurements by controlling the air pump or compressor 36 to provide static pressures p spanning a static pressure range, e.g. including ambient pressure $p_{amb}$, and determining the wideband acoustic immittance F(f, p), such as the complex acoustic admittance Y(f, p), the complex acoustic impedance Z(f, p), the complex acoustic reflectance Γ(f, p), the complex acoustic energy reflectance ER(f, p), the complex acoustic energy absorbance EA(f, p), or any other function that can be determined based on the output audio signal 30 and the input audio signal 26, as a function of frequency f and static pressure p based on the output audio signal 30 and the input audio signal 26 and the provided static pressure p.

The processor 28 may be adapted for identifying a middle ear resonance based on the determined wideband acoustic immittance F(f, p) in the same way as explained above for wideband acoustic immittance F(f) determined at ambient pressure $p_{amb}$, namely by identifying a possible middle ear resonance of possible one or more middle ear resonances based on the determined wideband acoustic immittance F(f, p) at a resonance frequency $f_{res}$ at which an acoustic admittance Y(f, p)=G(f, p)+jB(f, p) corresponding to, or calculated from, the determined wideband acoustic immittance F(f, p), fulfils that the conductance G($f_{res}$, p) is a global or local maximum of the conductance G(f, p) and that the gradient B'($f_{res}$, p) of the susceptance B(f, p) is a global or local minimum of the gradient B'(f, p).

The processor 28 may be adapted for performing the determination of wideband acoustic immittance F(f, p) applying static pressures p through the ear probe, such as static pressures of 0 daPa, TPP, 200 daPa, −400 daPa, etc.

Preferably, the processor 28 is adapted for determining the wideband acoustic admittance Y(f, p).

The processor 28 is adapted for performing baseline compensation, e.g. the processor 28 is adapted for determining a baseline compensated acoustic admittance $Y_{BC}(f, p_1, p_2) = Y_1(f, p_1) - Y_2(f, p_2)$ between a determined acoustic admittance $Y_1(f, p_1)$ as a function of frequency f at a first static pressure $p_1$ and a determined acoustic admittance $Y_2(f, p_2)$ as a function of frequency f at a second static pressure $p_2$, and identifying a middle ear resonance, if any, based on the baseline compensated acoustic admittance $Y_{BC}(f, p_1, p_2)$ by determining a first frequency $f_{res,1}$ and a second frequency $f_{res,2}$ at which the baseline compensated acoustic admittance $Y_{BC}(f, p_1, p_2) = Y_1(f, p_1) - Y_2(f, p_2)$ fulfils that the baseline compensated conductance $G_{BC}(f_{res,1}, p_1, p_2) = G_1(f_{res,1}, p_1) - G_2(f_{res,1}, p_2)$ of the baseline compensated acoustic admittance $Y_{BC}(f, p_1, p_2)$ is a local or global maximum and that the gradient $B'(f_{res,2}, p_1, p_2)$ of the baseline compensated acoustic susceptance $B_{BC}(f, p_1, p_2) = B_1(f, p_1) - B_2(f, p_2)$ is a local or global minimum and identifying a middle ear resonance when the absolute value of the difference between fres,1 and fres,2 is less than a threshold value determined by measurement inaccuracies and, optionally, some margin, such as 10%, such as 5%, such as 2%, of the first $f_{res,1}$ or second frequency $f_{res,2}$.

Corresponding baseline compensations may be performed for another immittance, such as the acoustic impedance Z(f), the acoustic reflectance Γ(f), the acoustic energy reflectance ER(f), the acoustic absorbance A(f), etc.

For example, a corresponding baseline compensated acoustic impedance $Z_{BC}(f, p_1, p_2)$ is given by:

$$Z_{BC}(f, p_1, p_2) = \frac{Z_1(f, p_1) * Z_2(f, p_2)}{Z_2(f, p_2) - Z_1(f, p_1)}$$

For example, the first static pressure $p_1$ may be the ambient pressure $p_{amb}$; or, the first static pressure $p_1$ may be the tympanic peak pressure TPP, etc.

For example, the second static pressure $p_2$ may be $p_{ref1}=200$ daPa; or, the second static pressure $p_2$ may be $p_{ref2}=-400$ daPa, etc.

The frequency range of the output audio signal, and thereby the emitted sound, may include the frequency range from 200 Hz-3 kHz.

The frequency range of the output audio signal, and thereby the emitted sound, may include the frequency range from 200 Hz-4 kHz.

The processor 28 is further adapted for controlling the display (not shown), e.g. a printer, a display screen, etc., to show a plot of the determined acoustic immittance F (f) and/or F (f, p) and/or $F_{BC}(f, p_1, p_2)$ with one or more identifications of corresponding one or more middle ear resonances.

Thus for the baseline compensated wideband acoustic immittance $F_{BC}(f, p_1, p_2)$, identification of possible middle ear resonance(s) may be performed in the same way as explained above for the wideband acoustic immittance F (f), but in the criteria for middle ear resonance identification, the wideband acoustic immittance F (f) is substituted with the baseline compensated wideband acoustic immittance $F_{BC}(f, p_2)$.

Figure 6:
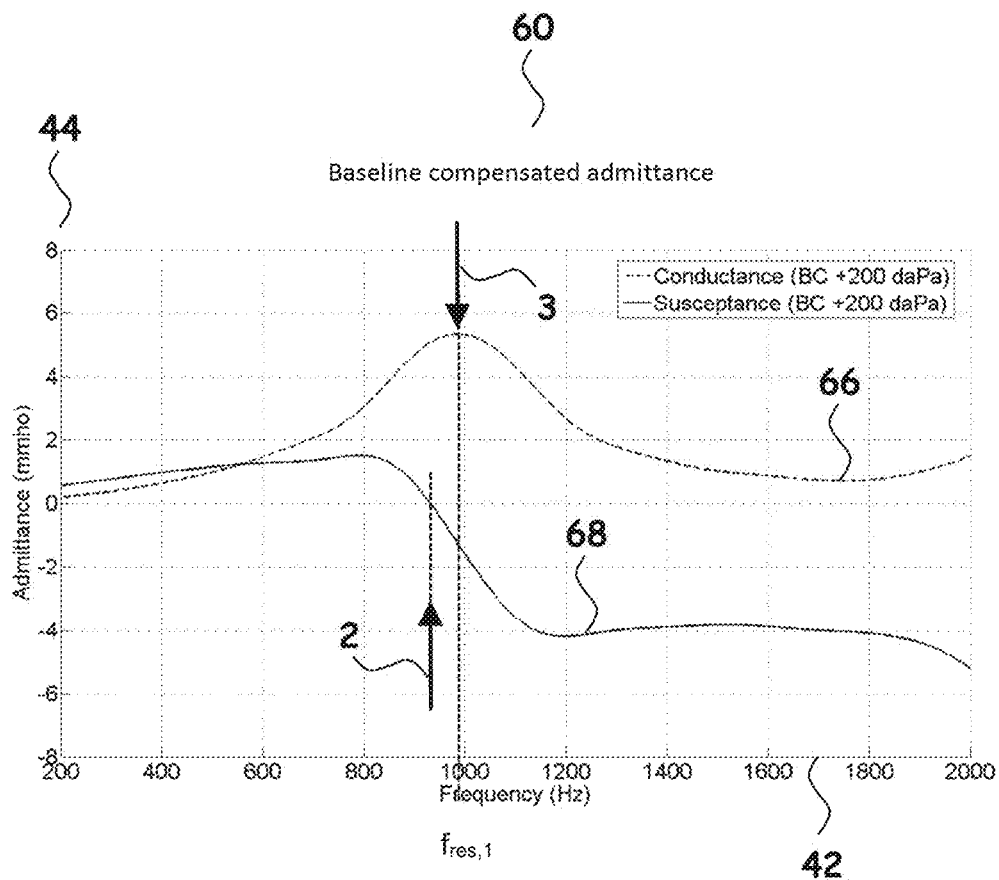
FIG. 6 shows an exemplary plot of baseline compensated conductance G(f) and susceptance B(f) for a real ear.

FIG. 6 shows an exemplary plot 60 of baseline compensated acoustic admittance $Y_{BC}(f, p_{ref1}) = Y(f, p_{amb}) - Y(f, p_{ref1})$ in which acoustic admittance $Y(f, p_{amb})$ is determined at ambient pressure $p_{amb}$ and acoustic admittance $Y(f, p_{ref1})$ is determined at a static pressure $p_{ref1}=+200$ daPa.

Frequency is plotted along the x-axis 42 and values in mmho of the baseline compensated conductance $G_{BC}(f, p_{ref1}) = G(f, p_{amb}) - G(f, p_{ref1})$ and baseline compensated susceptance $B_{BC}(f, p_{ref1}) = B(f, p_{amb}) - B(f, p_{ref1})$ are plotted along the y-axis 44.

The dashed curve 66 shows a plot of the baseline compensated conductance $G_{BC}(f, p_{ref1})$, and the solid curve 48 shows determined values of the baseline compensated susceptance $B_{BC}(f, p_{ref1})$.

In the plot 60, one middle ear resonance has been identified and marked by arrow 3 displayed on the display. The first frequency $f_{res,1}$ at which the processor 28 has determined a global maximum of the baseline compensated conductance $G_{BC}(f, p_{ref1})$ 66 is also shown. the second frequency $f_{res,2}$ at which the processor 28 has determined a global minimum of the baseline compensated susceptance $B_{BC}(f, p_{ref1})$ is not indicated. The distance between $f_{res,1}$ and $f_{res,2}$ was less than 10 Hz and is not shown.

According to conventional tympanometry, a middle ear resonance is determined at a frequency at which the baseline compensated susceptance $B_{BC}(f, p_{ref1}) = B(f, p_{amb}) - B_{EC}(f, p_{ref1})$ is equal to zero, which is indicated with arrow 2 in FIG. 6.

It should be noted that in some cases, one of which is illustrated in FIG. 6, the frequency determined by conventional tympanometry is different from the frequency $f_{res,1}$ at which the processor 28 is adapted for identifying a middle ear resonance based on the criteria that the baseline compensated conductance $G_{BC}(f, p_{ref1}) = G(f, p_{amb}) - G(f, p_{ref1})$ has a global maximum and that the gradient of the baseline compensated susceptance $B_{BC}(f, p_{ref1}) = B(f, p_{amb}) - B(f, p_{ref1})$ has a global minimum, which is indicated with arrow 3 in FIG. 6.

Figure 7:
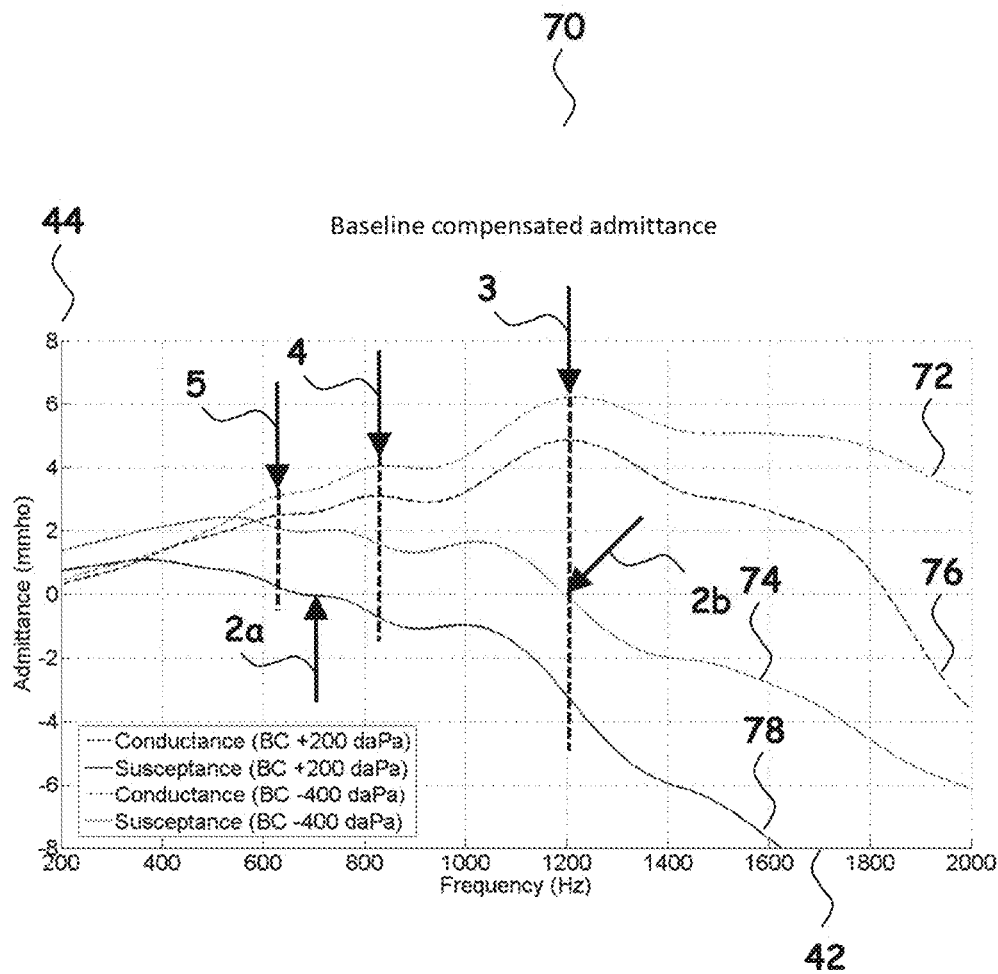
FIG. 7 shows baseline compensated conductance G(f) and susceptance B(f) recorded at static pressures of +200 daPa and −400 daPa.

FIG. 7 shows a plot 70 of baseline compensated conductances $G_{BC}(f, p_{ref1}, p_{ref2})$ 72, 76 and susceptances $B_{BC}(f, p_{ref1}, p_{ref2})$ 74, 78.

To obtain the plot 70, the processor 28 controls the air pump to adjust the static pressure in the ear canal 100 to be equal to the tympanic peak pressure TPP and determine conductance G(f, TPP) and susceptance B(f, TPP) as a function of frequency f.

Then, the processor 28 controls the air pump to adjust the static pressure p in the ear canal 100 to be equal to a reference pressure of $p_{ref1}=+200$ daPa and determine conductance $G(f, p_{ref1})$ and susceptance $B(f, p_{ref1})$ as a function of frequency f.

In the plot 70, the determined acoustic admittance $Y(f, p_{ref1})$ at the referenced pressure $p_{ref1}=+200$ daPa is subtracted from the acoustic admittance determined at TPP forming the baseline compensated acoustic admittance $Y_{BC}(f, TPP, p_{ref1})$ with reference pressure $p_{ref1}=+200$ daPa:

$Y_{BC1}(f) = Y_{BC}(f, TPP, p_{ref1}) = Y(f, TPP) - Y(f, p_{ref1})$ and $G_{BC1}(f) = G_{BC}(f, TPP, p_{ref1}) = G(f, TPP) - G(f, p_{ref1})$ $B_{BC1}(f) = B_{BC}(f, TPP, p_{ref1}) = B(f, TPP) - B(f, p_{ref1})$.

Further, the processor 28 controls the air pump to adjust the static pressure p in the ear canal 100 to be equal to a reference pressure of $p_{ref2}=-400$ daPa and determine conductance $G(f, p_{ref2})$ and susceptance $B(f, p_{ref2})$ as a function of frequency f.

In the plot 70, the determined acoustic admittance Y(f, $p_{ref2}$) at the reference pressure $p_{ref2}$=−400 daPa is subtracted from the acoustic admittance Y(f, TPP) determined at TPP forming the baseline compensated acoustic admittance $Y_{BC}$(f)=Y(f, TPP)−Y(f, $p_{ref2}$) with reference pressure $p_{ref2}$=−400 daPa:

$Y_{BC2}(f)=Y_{BC}(f,\text{TPP},p_{ref2})=Y(f,\text{TPP})-Y(f,p_{ref2})$ and $G_{BC2}(f)=G_{BC}(f,\text{TPP},p_{ref2})=G(f,\text{TPP})-G(f,p_{ref2})$ and $B_{BC2}(f)=B_{BC}(f,\text{TPP},p_{ref2})=B(f,\text{TPP})-B(f,p_{ref2})$.

In FIG. 7, frequency is plotted along the x-axis 42 and magnitude in mmho of the baseline compensated conductance $|G_{BC}(f)|$ and susceptance $|B_{BC}(f)|$ is plotted along the y-axis 44. The upper dashed curve 72 is the baseline compensated conductance $G_{BC1}(f)$ and the upper solid curve 74 is the baseline compensated susceptance $B_{BC1}(f)$. The lower dashed curve 76 is the baseline compensated conductance $G_{BC2}(f)$ and the lower solid curve 78 is the baseline compensated susceptance $B_{BC2}(f)$.

The middle ear resonances identified by conventional tympanometry, namely the frequencies at which the baseline compensated susceptances $B_{BC1}(f)$ and $B_{BC2}(f)$ are equal to zero, are marked with arrows 2a and 2b, respectively. The large distance along the frequency axis 42 between arrows 2a and 2b illustrates the dependence on reference pressures $p_{ref1}$ and $p_{ref2}$ when using conventional baseline compensation.

As opposed to this, the processor 28 has identified one middle ear resonance marked with arrow 3, which is the same for both baseline compensated admittances $Y_{BC1}(f)$ and $Y_{BC2}(f)$, i.e. independent of the static pressures $p_{ref1}$ and $p_{ref2}$. i.e. at the arrow 3 both baseline compensated conductances $G_{BC1}(f)$ and $G_{BC2}(f)$ have a global maximum and both gradients of the baseline compensated susceptances $B_{BC1}(f)$ and $B_{BC2}(f)$ have a global minimum.

Further, the processor 28 has identified two further middle ear resonances marked with arrows 4 and 5, respectively, that also coincide for the two baseline compensated admittances $Y_{BC1}(f)$ and $Y_{BC2}(f)$.

The processor 28 has identified a primary middle ear resonance 3 at app. 1200 Hz and a secondary middle ear resonance 4 at app. 800 Hz and a third middle ear resonance at app. 600 Hz.

Thus, FIG. 7 illustrates several important advantages of the new wideband acoustic immittance measurement apparatus 10, namely its capability of identifying middle ear resonances independent of the selected reference pressure of the baseline compensation, and its capability of identifying several middle ear resonances for further characterization of the middle ear subjected to the measurements.

The middle ear resonances of the determined wideband acoustic immittance F (f, p) may be detected using simple peak detection methods and/or polynomial fits.

The new wideband acoustic immittance measurement apparatus provides robust identification of middle ear resonances that is independent of which reference static pressure $p_{ref1}$, $p_{ref2}$ is used for baseline compensation, if any.

Figure 8:
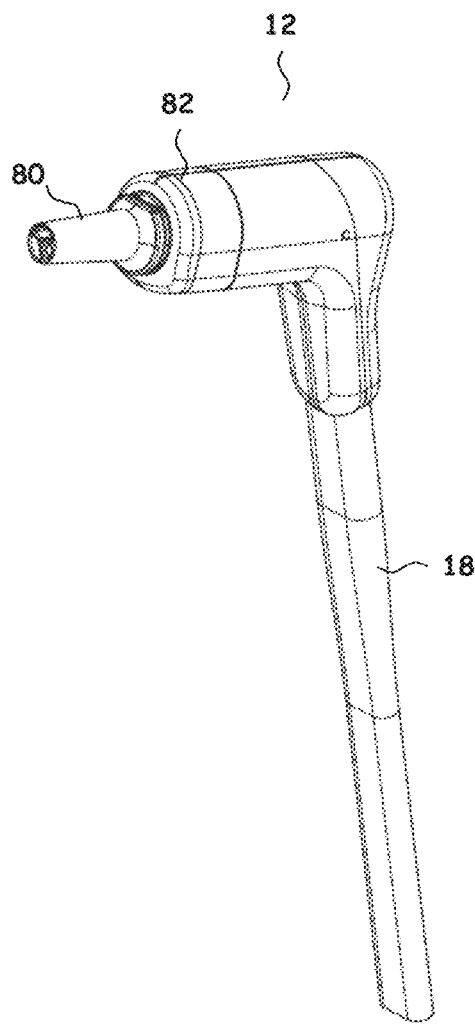
FIG. 8 schematically shows a perspective view of an ear probe of the wideband acoustic immittance measurement apparatus.

FIG. 8 shows schematically and in perspective a handheld ear probe 12 with a probe housing 82 and configured for connection with the new wideband acoustic immittance measurement apparatus 10

The probe housing 82 accommodates a lamp (not visible) configured to indicate measurement status, such as measurement is in progress, air leakage, instability of the measured ear cavity volume, etc.

During testing with the new wideband acoustic immittance measurement apparatus 10, the ear probe 12 is connected with a cable 18 to the new wideband acoustic immittance measurement apparatus 10 in a well-known way. The cable 18 includes electrical conductors (not visible) for interconnection of the microphone (not visible) and the loudspeaker (not visible) and the mechanically non-latching switch 86 and lamp (not visible) accommodated in the probe housing 82. The cable also 18 has an air conduit (not visible) for interconnection with the pump (not shown) in the housing 14 of the new wideband acoustic immittance measurement apparatus 10 for control of the static pressure in the ear canal 100.

The ear probe 12 comprises a conventional ear probe tip 80 preferably configured for fitting with an ear tip (not shown) for insertion into the ear canal 100 of the human and for sealing the ear canal 100 with an air tight seal. The probe tip 80 is connected with the air conduit of the cable 18 and the pump (not shown) of the new wideband acoustic immittance measurement apparatus 10. The ear tip may be disposable and for example made of rubber.

The results of the ear measurements performed with the new wideband acoustic immittance measurement apparatus 10 with the ear probe 12 are recorded by the new wideband acoustic immittance measurement apparatus 10 and stored in a memory of the wideband acoustic immittance measurement apparatus 10. The results are stored together with an indication of whether the right ear or the left ear was subject to the testing as selected with the user interface 32.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

What is claimed is:

1. A wideband acoustic immittance measurement apparatus for determination of wideband acoustic immittance in an ear of a human, comprising:
   an ear probe configured to be inserted in the ear of the human and having:
      an acoustic output port configured to emit sound into the ear of the human; and
      an acoustic input port configured to receive sound in the ear of the human, and a loudspeaker that is acoustically connected with the acoustic output port of the ear probe for emission of the sound;
   a microphone that is acoustically connected with the acoustic input port of the ear probe for generation of an input audio signal as a function of sound pressure at the acoustic input port; and
   a processor that is adapted for:
      providing an output audio signal to the loudspeaker for conversion into sound spanning a frequency range, and
      receiving the input audio signal generated by the microphone,
      determining wideband acoustic immittance F(f) as a function of frequency f based on the output audio signal and the input audio signal,
      identifying a middle ear resonance based on the determined wideband acoustic immittance F(f).

2. The wideband acoustic immittance measurement apparatus according to claim 1, wherein the middle ear resonance is identified based on the determined wideband acoustic admittance F(f) at a resonance frequency $f_{res}$ at which an acoustic admittance Y(f)=G(f)+jB(f) corresponding to the determined wideband acoustic immittance F(f) fulfils that a conductance $G(f_{res})$ is a maximum of a conductance G(f) and that a gradient $B'(f_{res})$ of a susceptance B(f) is a minimum of a gradient B'(f), where j is $\sqrt{-1}$.

3. The wideband acoustic immittance measurement apparatus according to claim 1, wherein the determined wideband acoustic immittance F(f) is selected from the group consisting of:
   i) acoustic admittance Y(f)=G(f)+jB(f)=|Y(f)|$e^{j\phi(f)}$ as a function of the frequency f, where G(f) is a conductance of Y(f) and jB(f) is a susceptance of Y(f);
   ii) acoustic impedance Z(f)=R(f)+j*X(f)=|Z(f)|$e^{j\theta(f)}$ as a function of the frequency f, wherein R(f) is a resistance of Z(f) and X(f) is a reactance of Z(f);
   iii) acoustic reflectance $$\Gamma(f) = \frac{z(f) - z_c(f)}{z(f) + z(f)}$$

as a function of the frequency f, wherein Zc is a characteristic impedance of an ear canal of the ear; and
   iv) acoustic absorbance A(f)=1−|Γ(f)|$^0$ as a function of the frequency f.

4. The wideband acoustic immittance measurement apparatus according to claim 3, wherein the processor is adapted for identifying a plurality of middle ear resonances of the determined wideband acoustic immittance F(f) at a corresponding plurality of resonance frequencies $f_{res,I}$, wherein at each resonance frequency $f_{res,I}$ the acoustic admittance Y(f)=G(f)+jB(f) corresponding to the determined wideband acoustic immittance F(f) fulfils that a conductance $G(f_{res,i})$ is a maximum of a conductance G(f) and a gradient $B'(f_{res,i})$ of a susceptance B(f) is a minimum of the gradient B'(f).

5. The wideband acoustic immittance measurement apparatus according claim 3, wherein:
   the determined wideband acoustic immittance F(f) is the acoustic admittance Y(f)=G(f)+jB(f); and
   the processor is adapted for identifying the middle ear resonance at a resonance frequency $f_{res}$ at which the acoustic admittance Y(f)=G(f)+jB(f) fulfils that a conductance $G(f_{res})$ is a maximum of a conductance G(f) and that a gradient $B'(f_{res})$ of a susceptance B(f) is a minimum of a gradient B'(f).

6. The wideband acoustic immittance measurement apparatus according to claim 2, wherein the processor is adapted for identifying a middle ear resonance of the determined wideband acoustic immittance F(f) at a resonance frequency $f_{res}$ at which the acoustic admittance Y(f)=G(f)+jB(f) corresponding to the determined wideband acoustic immittance F(f) fulfils that a magnitude |Y($f_{res}$)| of the acoustic admittance Y(f) is a maximum of a magnitude |Y(f)| and that a gradient $\phi'(f_{res})$ of a phase $\phi(f)$ is a minimum of a gradient $\phi'(f)$.

7. The wideband acoustic immittance measurement apparatus according to claim 6, wherein the determined wideband acoustic immittance F(f) is selected from the group consisting of:
   i) acoustic admittance Y(f)=G(f)+jB(f)=|Y(f)|$e^{j\phi(f)}$ as a function of the frequency f, wherein $\phi(f)$ is a phase of Y(f);
   ii) acoustic impedance Z(f)=R(f)+j*X(f)=|Z(f)|$e^{j\theta(f)}$ as a function of the frequency f, wherein R(f) is a resistance of Z(f), X(f) is a reactance of Z(f), and $\theta(f)$ is a phase of Z(f);
   iii) acoustic reflectance $$\Gamma(f) = \frac{z(f) - z_c(f)}{z(f) + z(f)}$$

as a function of the frequency f, wherein Zc is a characteristic impedance of an ear canal of the ear; and
   iv) acoustic absorbance A(f)=1−|Γ(f)|$^0$ as a function of the frequency f.

8. The wideband acoustic immittance measurement apparatus according to claim 7, wherein the processor is adapted for identifying a plurality of middle ear resonances of the determined wideband acoustic immittance F(f) at a corresponding plurality of resonance frequencies $f_{res,i}$, wherein at each resonance frequency $f_{res,i}$ the acoustic admittance Y(f)=G(f)+jB(f) corresponding to the determined wideband acoustic immittance F(f) fulfils that a conductance $G(f_{res,i})$ is a maximum of the conductance G(f) and a gradient $B'(f_{res,i})$ of the susceptance B(f) is a minimum of the gradient B'(f).

9. The wideband acoustic immittance measurement apparatus according claim 7, wherein:
   the determined wideband acoustic immittance F(f) is the acoustic admittance Y(f)=G(f)+jB(f); and
   the processor is adapted for identifying the middle ear resonance at the resonance frequency $f_{res}$ at which the acoustic admittance Y(f)=G(f)+jB(f) fulfils that the conductance $G(f_{res})$ is the maximum of the conductance G(f) and that the gradient $B'(f_{res})$ of the susceptance B(f) is a minimum of the gradient B'(f).

10. The wideband acoustic immittance measurement apparatus according to claim 1, wherein the processor is adapted for determining a parameter of the wideband acoustic immittance F(f) at the middle ear resonance of the determined wideband acoustic immittance F (f).

11. The wideband acoustic immittance measurement apparatus according to claim 10, wherein the determined wideband acoustic immittance F(f) is selected from the group consisting of:
   i) acoustic admittance Y(f)=G(f)+jB(f)=|Y(f)|$e^{j\phi(f)}$ as a function of the frequency f, where G(f) is a conductance of Y(f) and jB(f) is a susceptance of Y(f);
   ii) acoustic impedance Z(f)=R(f)+j*X(f)=|Z(f)|$e^{j\theta(f)}$ as a function of the frequency f;
   iii) acoustic reflectance $$\Gamma(f) = \frac{z(f) - z_c(f)}{z(f) + z(f)}$$

as a function of the frequency f, wherein Zc is a characteristic impedance of an ear canal of the ear; and
   iv) acoustic absorbance A(f)=1−|Γ(f)|$^0$ as a function the of frequency f.

12. The wideband acoustic immittance measurement apparatus according to claim 10, wherein the processor is adapted for identifying a plurality of middle ear resonances of the determined wideband acoustic immittance F(f) at a corresponding plurality of resonance frequencies $f_{res,I}$, wherein at each resonance frequency $f_{res,I}$ the acoustic admittance Y(f)=G(f)+jB(f) corresponding to the determined wideband acoustic immittance F(f) fulfils that a conductance $G(f_{res,i})$ is a maximum of a conductance $G(f)$ and a gradient $B'(f_{res,i})$ of a susceptance $B(f)$ is a minimum of a gradient $B'(f)$.

13. The wideband acoustic immittance measurement apparatus according claim 10, wherein:
   the determined wideband acoustic immittance $F(f)$ is an acoustic admittance $Y(f)=G(f)+jB(f)$; and
   the processor is adapted for identifying the middle ear resonance at a resonance frequency $f_{res}$ at which the acoustic admittance $Y(f)=G(f)+jB(f)$ fulfils that a conductance $G(f_{res})$ is a maximum of a conductance $G(f)$ and that a gradient $B'(f_{res})$ of a susceptance $B(f)$ is a minimum of a gradient $B'(f)$.

14. The wideband acoustic immittance measurement apparatus according to claim 10, wherein the parameter of the wideband acoustic immittance $F(f)$ at the middle ear resonance is selected from the group consisting of a magnitude of a conductance $G(f_{res})$, a magnitude of a minimum of a gradient of a susceptance $B'(f_{res})$.

15. The wideband acoustic immittance measurement apparatus according claim 1, wherein:
   the determined wideband acoustic immittance $F(f)$ is an acoustic admittance $Y(f)=G(f)+jB(f)$, where $G(f)$ is a conductance of $Y(f)$ and $jB(f)$ is a susceptance of $Y(f)$; and
   the processor is adapted for identifying the middle ear resonance at a resonance frequency $f_{res}$ at which the acoustic admittance $Y(f)=G(f)+jB(f)$ fulfils that a magnitude $|Y(f_{res})|$ of the acoustic admittance $Y(f)$ is a maximum of a magnitude $|Y(f)|$ and that a gradient $\phi'(f_{res})$ of a phase $\phi(f)$ is a minimum of a gradient $\phi'(f)$.

16. The wideband acoustic immittance measurement apparatus according to claim 1, the apparatus further comprising:
   a housing for accommodation of an air pump;
   wherein the ear probe comprises an ear probe air conduit for connection with the air pump and having an air output for applying a static pressure p to an ear canal of an ear through an ear tip air conduit of an ear tip configured to be inserted into the ear canal of the human and for sealing the ear canal with an air tight seal; and
   wherein the processor is adapted for controlling the air pump to provide the static pressures p spanning a pressure range, and determining a wideband acoustic immittance $F(f, p)$ as a function of the frequency f and the static pressure p based on the output audio signal and the input audio signal and the provided static pressure p.

17. The wideband acoustic immittance measurement apparatus according to claim 1, wherein the processor is adapted for:
   determining a baseline compensated acoustic admittance $Y_{BC}(f, p_1, p_2)=Y_1(f, p_1)-Y_2(f, p_2)$ between a determined acoustic admittance $Y_1(f, p_1)$ as a function of frequency f at a first static pressure $p_1$ and a determined acoustic admittance $Y_2(f, p_2)$ as a function of frequency f at a second static pressure $p_2$; and
   identifying a middle ear resonance based on the baseline compensated acoustic admittance $Y_{BC}(f, p_1, p_2)$ by determining a first frequency $f_{res,1}$ and a second frequency $f_{res,2}$ at which the baseline compensated acoustic admittance $Y_{BC}(f, p_1, p_2)=Y_1(f, p_1)-Y_2(f, p_2)$ fulfils that a baseline compensated conductance $G_{BC}(f_{res,1}, p_1, p_2)=G_1(f_{res,1}, p_1)-G_2(f_{res,1}, p_2)$ of the baseline compensated acoustic admittance $Y_{BC}(f, p_1, p_2)$ is a local or global maximum and that a gradient $B'(f_{res,2}, p_1, p_2)$ of a baseline compensated acoustic susceptance $B_{BC}(f, p_1, p_2)=B_1(f, p_1)-B_2(f, p_2)$ is a local or global minimum and identifying a middle ear resonance when an absolute value of a difference between fres,1 and fres,2 is less than a threshold value.

18. The wideband acoustic immittance measurement apparatus according claim 1 wherein the frequency range of the output audio signal includes a range from 200 Hz-3 kHz.

19. The wideband acoustic immittance measurement apparatus according claim 1 wherein the frequency range of the output audio signal includes a range from 200 Hz-4 kHz.

20. The wideband acoustic immittance measurement apparatus according claim 19 wherein the frequency range of the output audio signal includes a range from 200 Hz-3 kHz.

* * * * *